US008121856B2

(12) United States Patent
Huster et al.

(10) Patent No.: US 8,121,856 B2
(45) Date of Patent: *Feb. 21, 2012

(54) REMOTE ACCESS TO HEALTHCARE DEVICE DIAGNOSTIC INFORMATION

(75) Inventors: Keith A. Huster, Sunman, IN (US);
Patricia A. Glidewell, Apex, NC (US);
James M. Allen, Batesville, IN (US);
Williams F. Collins, Jr., Columbus, IN (US); Carl William Riley, Milan, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 1061 days.

This patent is subject to a terminal disclaimer.

(21) Appl. No.: 11/426,709

(22) Filed: Jun. 27, 2006

(65) Prior Publication Data

US 2007/0010719 A1  Jan. 11, 2007

Related U.S. Application Data

(60) Provisional application No. 60/694,713, filed on Jun. 28, 2005.

(51) Int. Cl.
*G06Q 10/00* (2006.01)
(52) U.S. Cl. ................................. 705/2; 705/3
(58) Field of Classification Search .................. 705/2, 3
See application file for complete search history.

(56) References Cited

U.S. PATENT DOCUMENTS

| | | |
|---|---|---|
| 4,183,015 A | 1/1980 | Drew et al. |
| 4,539,560 A | 9/1985 | Fleck et al. |
| 4,601,064 A | 7/1986 | Shipley |
| 4,838,275 A | 6/1989 | Lee |
| 4,967,195 A | 10/1990 | Shipley |
| 5,062,151 A | 10/1991 | Shipley |
| 5,291,399 A | 3/1994 | Chaco |
| 5,455,851 A | 10/1995 | Chaco et al. |
| 5,465,082 A | 11/1995 | Chaco |
| 5,515,426 A | 5/1996 | Yacenda et al. |
| 5,537,095 A | 7/1996 | Dick et al. |
| 5,561,412 A | 10/1996 | Novak et al. |
| 5,594,786 A | 1/1997 | Chaco et al. |
| 5,689,229 A | 11/1997 | Chaco et al. |
| 5,699,038 A | 12/1997 | Ulrich et al. |
| 5,715,548 A | 2/1998 | Weismiller et al. |
| 5,771,511 A | 6/1998 | Kummer et al. |
| 5,822,418 A | 10/1998 | Yacenda et al. |
| 5,822,544 A | 10/1998 | Chaco et al. |
| 5,838,223 A | 11/1998 | Gallant et al. |
| 6,005,486 A | 12/1999 | Fridley et al. |
| 6,008,736 A | 12/1999 | Palm et al. |

(Continued)

*Primary Examiner* — Robert Morgan
*Assistant Examiner* — Maroun Kanaan
(74) *Attorney, Agent, or Firm* — Barnes & Thornburg LLP

(57) ABSTRACT

A method and system for remote diagnostic monitoring of a healthcare device, for example, a patient support system. The system includes a communication device configured to transmit sensor data received from a sensor system coupled to the patient support system and configured to generate sensor data relating to diagnostic information of the healthcare device. The communication device can also be configured to receive configuration data for configuring at least one of the healthcare device and the sensor system. The monitoring device is located geographically distant from the healthcare device, is coupled to the communication adapter by a datalink, for example, a telecommunication network, and is configured to receive the sensor data. The monitoring device is configured to determine, based on the received data, whether service or replacement of the healthcare device or a portion thereof is indicated.

20 Claims, 26 Drawing Sheets

U.S. PATENT DOCUMENTS

| | | |
|---|---|---|
| 6,009,333 A | 12/1999 | Chaco |
| 6,067,019 A | 5/2000 | Scott |
| 6,133,837 A | 10/2000 | Riley |
| 6,147,592 A | 11/2000 | Ulrich et al. |
| 6,208,250 B1 | 3/2001 | Dixon et al. |
| 6,212,256 B1 | 4/2001 | Miesbauer et al. |
| 6,279,183 B1 | 8/2001 | Kummer et al. |
| RE37,531 E | 1/2002 | Chaco et al. |
| 6,344,794 B1 | 2/2002 | Ulrich et al. |
| 6,353,445 B1 | 3/2002 | Babula et al. |
| 6,362,725 B1 | 3/2002 | Ulrich et al. |
| 6,366,328 B1 | 4/2002 | Vanderpohl, III et al. |
| 6,377,162 B1 | 4/2002 | Delestienne et al. |
| 6,381,557 B1 | 4/2002 | Babula et al. |
| 6,412,980 B1 | 7/2002 | Lounsberry et al. |
| 6,434,572 B2 | 8/2002 | Derzay et al. |
| 6,453,009 B2 | 9/2002 | Berezowitz et al. |
| 6,462,656 B2 | 10/2002 | Ulrich et al. |
| 6,494,831 B1 | 12/2002 | Koritzinsky |
| 6,539,393 B1 | 3/2003 | Kabala |
| 6,611,865 B1 | 8/2003 | Perugini et al. |
| 6,633,833 B2 | 10/2003 | Sharma et al. |
| 6,791,460 B2 | 9/2004 | Dixon et al. |
| 6,825,763 B2 | 11/2004 | Ulrich et al. |
| 6,847,918 B2 | 1/2005 | Loecher |
| 6,876,303 B2 | 4/2005 | Reeder et al. |
| 6,897,780 B2 | 5/2005 | Ulrich et al. |
| 6,957,461 B2 | 10/2005 | Osborne et al. |
| 6,958,706 B2 | 10/2005 | Chaco et al. |
| 7,009,511 B2 * | 3/2006 | Mazar et al. .................. 340/531 |
| 7,012,534 B2 | 3/2006 | Chaco |
| 7,034,690 B2 | 4/2006 | Chaco |
| 7,050,984 B1 | 5/2006 | Kerpelman et al. |
| 7,080,061 B2 | 7/2006 | Kabala |
| 7,080,095 B2 | 7/2006 | Accardi et al. |
| 7,092,376 B2 | 8/2006 | Schuman |
| 7,099,620 B2 | 8/2006 | Miller |
| 2001/0051787 A1 * | 12/2001 | Haller et al. .................... 604/66 |
| 2002/0014951 A1 | 2/2002 | Kramer et al. |
| 2002/0044059 A1 | 4/2002 | Reeder et al. |
| 2002/0151990 A1 * | 10/2002 | Ulrich et al. .................... 700/65 |
| 2003/0052787 A1 | 3/2003 | Zerhusen et al. |
| 2004/0138920 A1 * | 7/2004 | Sawanaga et al. ................ 705/2 |
| 2006/0122481 A1 * | 6/2006 | Sievenpiper et al. ......... 600/407 |

* cited by examiner

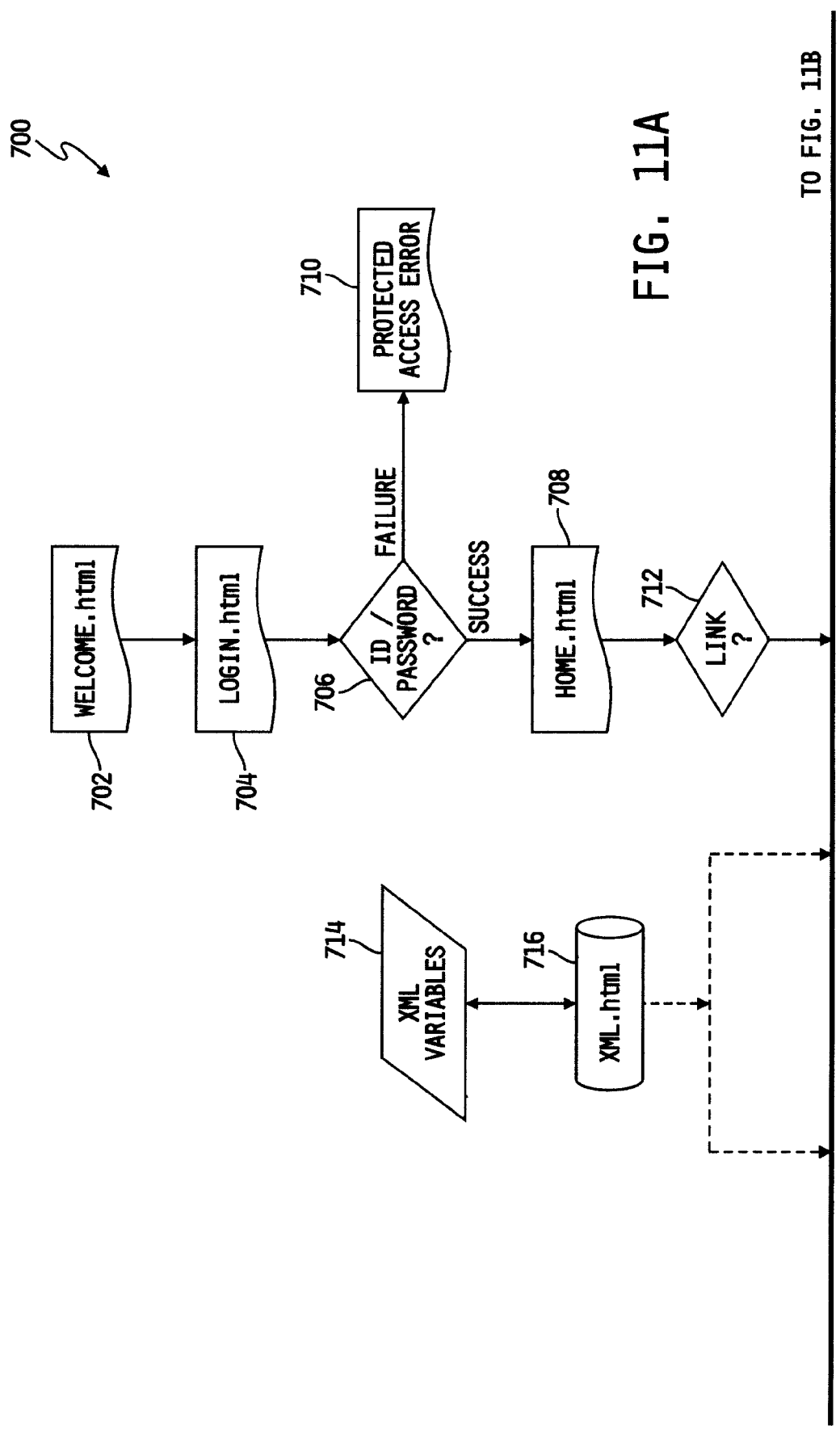

REMOTE ACCESS TO HEALTHCARE DEVICE DIAGNOSTIC INFORMATION

CROSS-REFERENCE TO RELATED APPLICATION

This application claims the benefit under 35 U.S.C. §119 (e) of U.S. Provisional Application Ser. No. 60/694,713, filed Jun. 28, 2005, which is expressly incorporated by reference herein.

BACKGROUND

The present invention relates to a monitoring system for a healthcare device, and particularly, to remote access of diagnostic information relating to a patient support system.

Healthcare devices, for example, patient support systems such as hospital beds, include many components and associated equipment which are subject to a limited predetermined number of cycles, wear and tear, and which require preventative or responsive service or replacement. In some cases such service or replacement is determined or even predicted by monitoring the data available from a sensor system associated with the healthcare device. For example, as a fault condition occurs or as the predetermined limited number of cycles of an actuator or other component is being approached, preventive service or replacement of the actuator or other component is indicated. In some devices, such information is available only at the device or locally in the facility where the device is located. Additionally, such diagnostic information may not be accessible until after a healthcare device in use actually fails or otherwise requires such service or replacement.

SUMMARY

The present invention may comprise one or more of the features recited in the attached claims, and/or one or more of the following features or combinations thereof.

An illustrative embodiment of a remote diagnostic monitoring system for a patient support system, includes a sensor system coupled to the patient support system and configured to generate sensor data relating to at least one parameter of the patient support system, a communication adapter coupled to the sensor system and configured to transmit the sensor data, and a monitoring device located geographically distant from the patient support system, coupled to the communication adapter by a first datalink, and configured to receive the sensor data and determine a diagnostic status of the patient support system based on the received sensor data. The first datalink may include at least one of a telecommunication network and the Internet. The system may have a second datalink coupling the sensor system and the communication adapter. The second datalink may include a wireless communication connection.

The communication adapter in one illustrative embodiment is configured to convert the sensor data from a first protocol used by the sensor system to a second protocol used by at least one of the first data link, the second data link, and the monitoring device. The second protocol may be an XML or TCP/IP protocol. The communication adapter may include a webserver or a network portal. The first datalink further may include a healthcare facility network and a server of the healthcare facility network.

The sensor data may relate to vibration, displacement, rate, component, temperature, ambient temperature, component humidity, ambient humidity, thermal loading, pressure, noise, mechanical load, current, voltage, electrical power, signal signature, calibration values, transit time, fault rate, logic or communication error, and/or accumulated usage. The sensor system may monitor a drive, a user control, a caregiver control, an air system, a movable member, a power supply, a battery, a load cell, control logic, a communication circuit, a sensor, and/or a cycle counter. The monitoring device may be configured to determine whether service or replacement of the healthcare device is indicated based on the sensor data. The monitoring device may be configured to determine a replacement component based on the sensor data. The monitoring device may be configured to transmit a message relating to service or replacement of the healthcare device to the healthcare facility where the healthcare device is located.

An illustrative embodiment of a communication adapter for transmitting diagnostic information between a patient support system and a remote monitoring device includes a first protocol converter coupled to the patient support system and configured for transmission and protocol conversion of diagnostic information between a first communication protocol used by the patient support system and a second communication protocol. The communication adapter may also have communication device configured to receive the diagnostic information and transmit the diagnostic information to the remote monitoring device. The communication adapter may also include a second protocol converter coupled to the first protocol converter and configured for transmission and protocol conversion of diagnostic information between the second communication protocol and a third communication protocol.

The diagnostic information may relate to at least one parameter of a component of the patient support system, and the at least one parameter may relate to vibration, displacement, rate, component temperature, ambient temperature, component humidity, ambient humidity, thermal loading, pressure, noise, mechanical load, current, voltage, electrical power, signal signature, calibration values, transit time, fault rate, logic or communication error, and/or accumulated usage. The diagnostic information may relate status of a drive, a user control, a caregiver control, an air system, a movable member, a power supply, a battery, a load cell, control logic, a communication circuit, a sensor, and/or a cycle counter.

An illustrative embodiment of a method of remotely monitoring a hospital bed, includes the steps of providing data relating to at least one parameter of the hospital bed, converting the data for transmission, transmitting the data over a telecommunication network, receiving the data at a geographically remotely located monitoring system, and determining based on the received data whether service or replacement of the hospital bed or a portion thereof is indicated. The method may further include the step of transmitting a message relating to service or replacement to one or more designated recipients at a healthcare facility where the hospital bed is located. The method may also include the step of transmitting to a healthcare asset management entity an order for one of service or replacement of the hospital bed.

The data may relate to an actuator, a temperature, a humidity, a current, a voltage, a battery charge, a communication failure, a component position, a cycle count for a component, a vibration, a displacement, a rate, a component temperature, an ambient temperature, a component humidity, an ambient humidity, a thermal loading, a pressure, a noise, a mechanical load, a current, a voltage, an electrical power, a signal signature, a calibration value, a transit time, a fault rate, a logic or communication error, an accumulated usage, a status of a drive, a user control, a caregiver control, an air system, a movable member, a power supply, a battery, a load cell, control logic, a communication circuit, a sensor, and/or a cycle counter.

Additional features of the disclosure will become apparent to those skilled in the art upon consideration of the following detailed description of the illustrative embodiment.

BRIEF DESCRIPTION OF THE DRAWINGS

The detailed description particularly refers to the accompanying figures in which:

FIGS. 11A and 11B a are flowchart of a software algorithm associated with the webserver interface of the system of FIG. 1 and for providing webpages for communicating and displaying the information received from the patient support system;

DESCRIPTION OF THE ILLUSTRATIVE EMBODIMENTS

Figure 1:
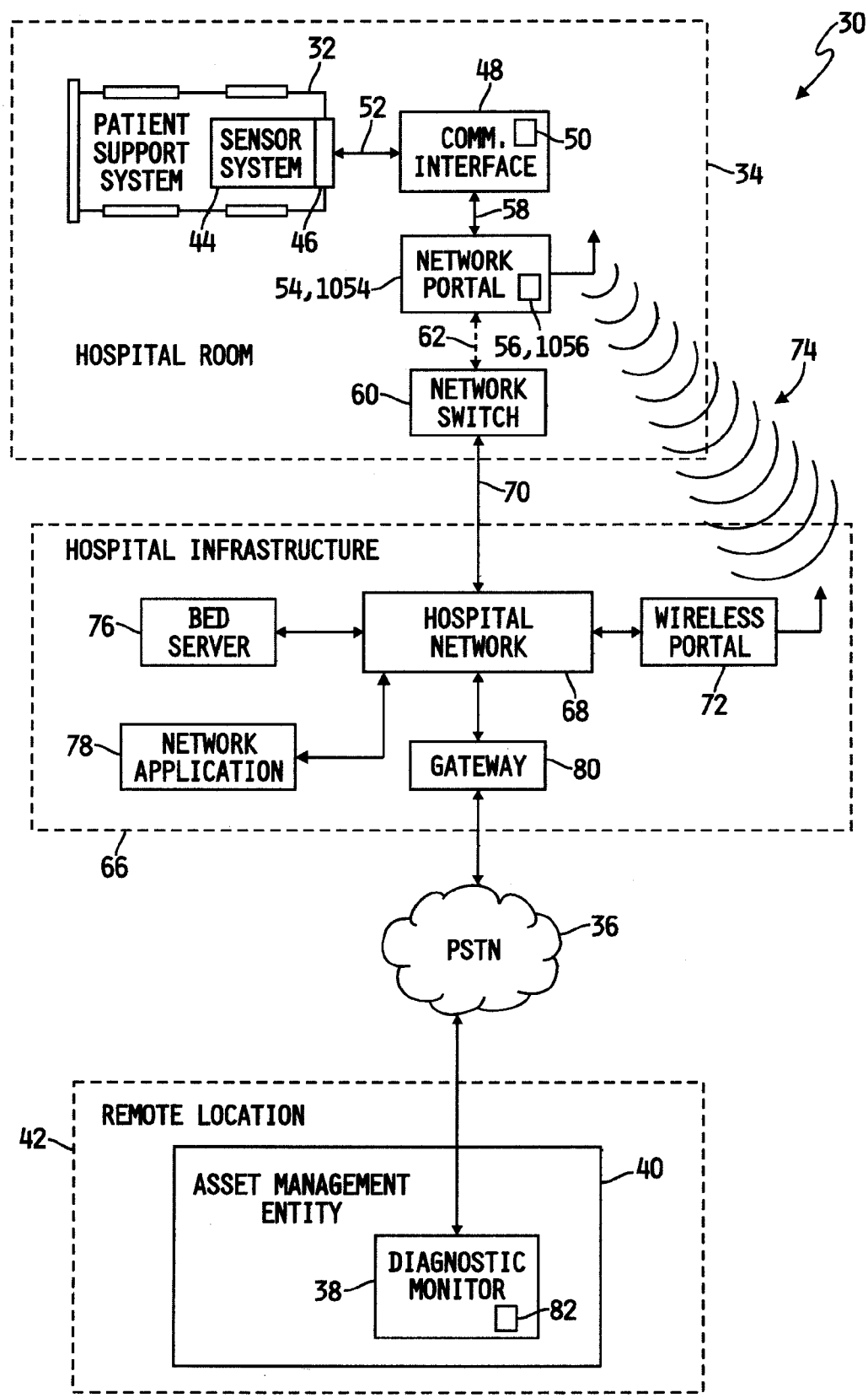
FIG. 1 is a block diagram of a remote monitoring system for a patient support system.

Referring to FIG. 1, an illustrative monitoring system 30 provides access to diagnostic information (alternatively referred to herein as "data") associated with a healthcare device, for example, a patient support system 32. The access to the data can be from a location 42 which is geographically remote relative to a hospital room 34, health care facility, or other location where the patient support system 32 is located. A monitoring device 38 located at the remote location 42 is configured to monitor diagnostic information that is provided by broadcast or by request.

Monitoring device 38 can also be configured to transmit configuration data or firmware to the patient support system 32 and associated devices. Additionally, the monitoring device 38 is configured to analyze diagnostic information received from the patient support system 32 and to determine whether service or replacement of a component of or the entire patient support system 32 is indicated. The monitoring device 38 can also be configured to order the indicated service or replacement, for example, from a medical equipment asset management entity 40, and to indicate the status of the service or replacement, and/or the status of the patient support system 32 to the hospital or other facility where the patient support system 32 is located. The monitoring device 38 may be located, for example, at the manufacturing, service or other support facility for the system 32. The monitoring device 32 can be co-located with or remotely located from asset management entity 40.

Patient support systems 32, for example, hospital beds such as those available from Hill-Rom of Batesville, Ind., generally include a sensor system 44. Sensor system 44 provides monitoring of parameters and/or the status of components and accessories associated with the patient support system 32. Sensor system 44 also provides control and communication with components and accessories of the patient support system 32, as will be discussed in more detail below.

In the illustrative embodiment, the patient support system 32 includes a bed communication device 46, which is coupled to the sensor system 44. The bed communication device 46 provides bidirectional communication with the sensor system 44, and can also provide communication for other components and aspects of the patient support system 32, for example, nurse call functions and lighting controls (not shown). In the illustrative embodiment, bed communication device 46 uses a current loop serial communication protocol, for example, the serial peripheral interface (SPI) protocol; however, other communication protocols may be used.

In the illustrative embodiment, a communication interface 48 is also associated with each patient support system 32. For example, the communication interface 48 can be mounted on or behind a wall (not shown) of the hospital room 34, or can be incorporated with the patient support system 32, for example, with sensor system 44 or bed communication device 46. The communication interface 48 includes a processor 50 and associated software, described in further detail below, for converting data received from the sensor system 44 via the communication device 46 from the bed communication protocol to another communication protocol, for example, RS-232. The communication interface 48 is be coupled with the bed communication device 46 by a wired or wireless datalink 52. The processor 50 can be, for example, an 8051 based microcontroller such as part number AT89C51RC2 available from Atmel of San Jose, Calif.

In the illustrative embodiment, one of either a webserver 54 or a network interface 1054 provides communication protocol conversion for the data received from communication interfaces 48 and enables communication of the data over a network, for example, a wide area network (WAN). For example, the network/webserver interface 54, 1054 includes a processor 56, 1056 and associated software and/or other hardware converting the received data from the protocol used by the communication interface 48, for example, RS-232, to a protocol suitable for transmission over a network. For example, webserver 54 can be configured to convert data to the Extensible Markup Language (XML) protocol, providing webpage access to the data of the associated patient support system 32. The webserver 54 can be, for example, part number NS7520 available from NetSilicon of Waltham, Mass. Alternatively, the network interface 1054 can provide Ethernet, TCP/IP, DHCP, or other networking protocols and other access to the data of the associated patient support system 32. The network interface 1054 can be, for example, an embedded wireless networking device server such as the WiPort (trademark of Lantronix) available from Lantronix of Irvine, Calif.

The illustrative embodiment of the monitoring system 30 shown in FIG. 1 also includes a network port or switch 60 for coupling the network/webserver interface 54, 1054 with a network, for example, a WAN such as a hospital network 68. However, the network switch 60 can alternatively or additionally directly or indirectly couple the network/webserver interface 54, 1054 to a telecommunications network, for example, a public switch telecommunications network (PSTN) 36, for example, the Internet or other telecommunications network. In the illustrative embodiment shown in FIG. 1, a wired datalink 62 couples the network/webserver interface 54, 1054 with the network switch 60, and a wired datalink 70 couples the network switch 70 with the hospital network 68. Alternatively, as shown in FIG. 1, the interface 54, 1054 includes a wireless portal so that a wireless datalink 74 is used to couple the interface 54, 1054 with a wireless portal 72, which is coupled to the hospital network 68. The wireless datalink 74 also can be used to transmit data to other wireless devices, for example, a handheld portable digital assistant (PDA).

The hospital infrastructure 66 can also include other components in addition to the hospital network 68 and the wireless portal 72. For example, an internet gateway 80 couples the hospital network 68 with the PSTN 36. Other examples of components of the hospital infrastructure 66 include a bed server 76 and a network application 78, which are more fully described in U.S. application Ser. No. 11/189,781, which was filed Jul. 27, 2005, is assigned to the assignees of the present application, and is incorporated expressly herein by reference. The bed server 76 can be configured to poll, receive broadcasts from, or otherwise receive the diagnostic information transmitted by the communication interface 48. Similarly, the network application 78, for example, a nurse call management software system, such as the OnSite (trademark of Hill-Rom) system available from Hill-Rom, also can be configured to poll, receive broadcasts from, or otherwise receive the diagnostic information. For example, the network application can be configured to receive the diagnostic information, or signals that are a function of the diagnostic information, from the bed server 76 or another device having connectivity with the hospital network 68. The monitoring device 38, for example, a computer or other device having a processor 82 and associated software, and the asset management entity 40, for example, MEDIQ of Pennsauken, N.J., also polls or otherwise receives diagnostic information from the communication interface 48. In some embodiments, the diagnostic information received by monitoring device 38 is first collected by another device and then retransmitted to the monitoring device 38, for example, by the bed server 76.

The various communication devices 46, 48, 54, 1054, 60, 80, and networks 68 and 36 are bi-directional so that the monitoring device 38 can also send data to the patient support system 32. For example, the monitoring device 38 can poll or request specific data from the sensor system 44 or transmit configuration data to the patient support system 32, for example, updated firmware for the bed communication device 46, the sensor system 44, or other components of the patient support system 32.

The datalinks 52, 58, 62, 70 and 74 coupling the communication devices 46, 48, 54, 1054, 60 and 68 are wired or wireless connections. For example, in the illustrative embodiment, datalink 74 providing communication between the bed communication device 46 and the communication interface 48 is a wired or wireless connection, for example, WIMAX IEEE 802.16, WIFI IEEE 802.11, or other wireless protocols.

Figure 2A:
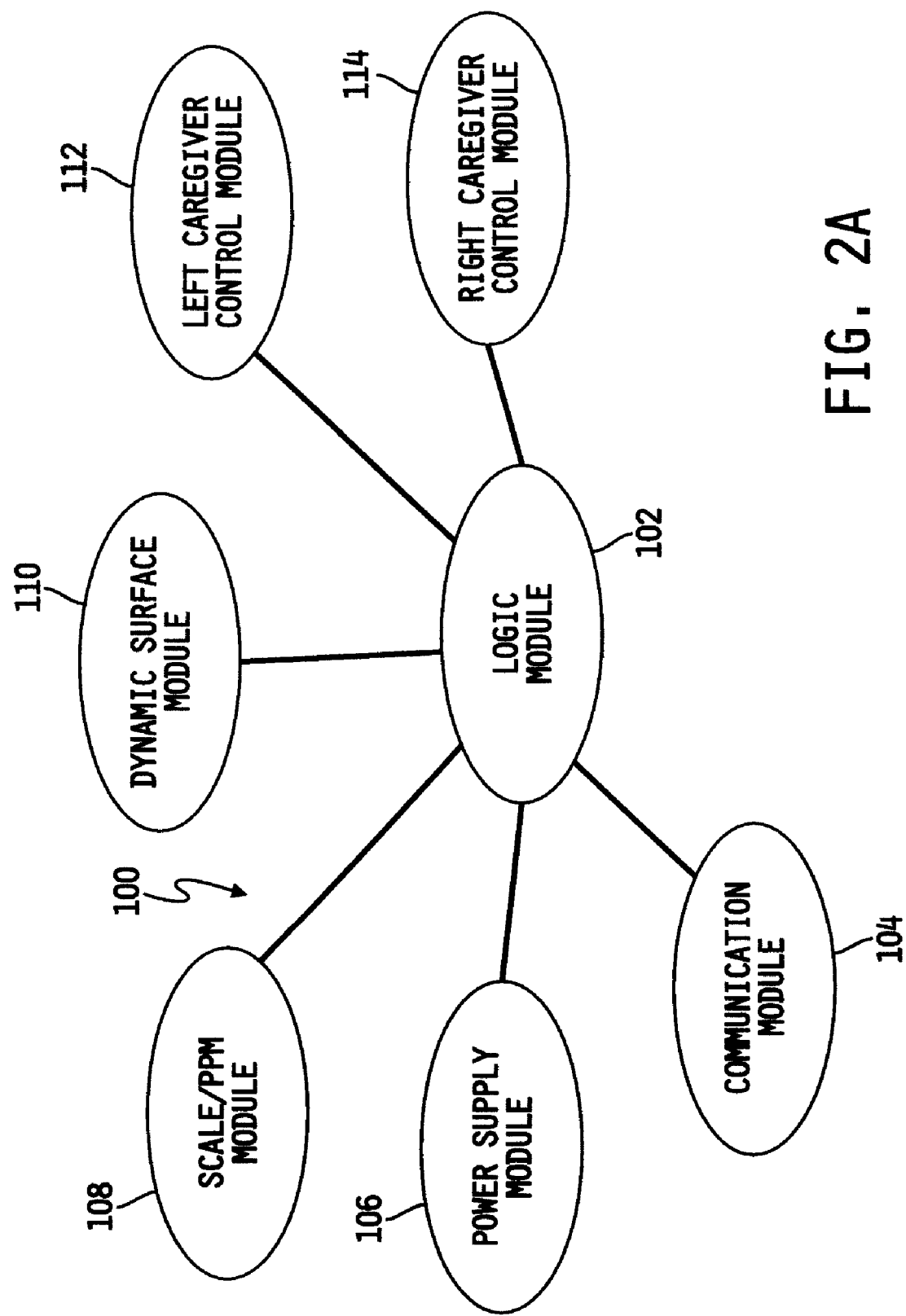
FIG. 2A-2E are block diagrams of the control and communication systems and associated components of the patient support system of FIG. 1.
Figure 2B:
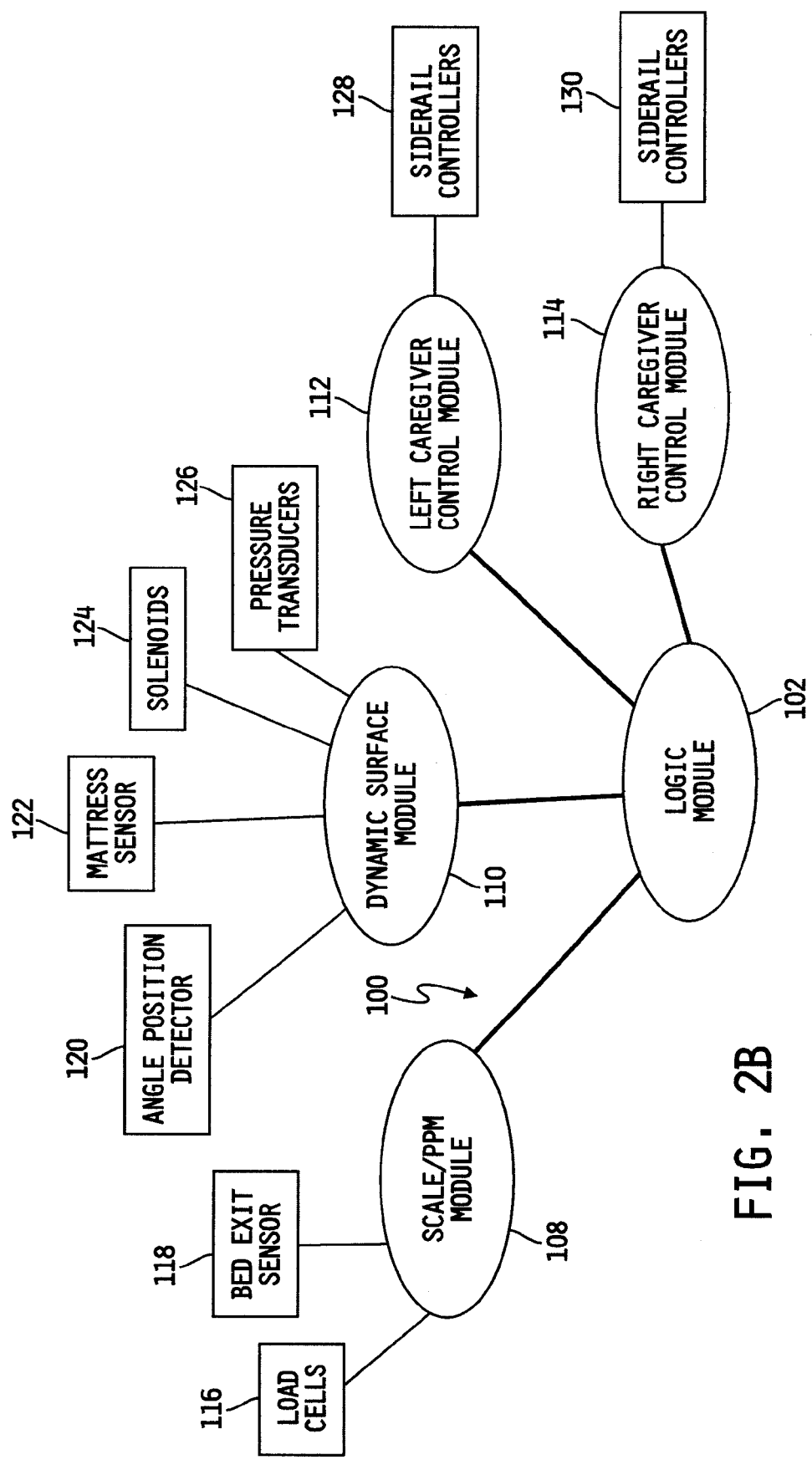

Referring now to FIGS. 2A-2B, block diagrams of the control and communications systems and associated components of the patient support system 32 are shown. According to this disclosure, sensor system 44 can include or be associated with any or all of the systems and components shown in FIGS. 2A-2E and described below. The illustrative bed network 100 is a controller area network (CAN) having a serial bus connecting each of seven modules for controlling and monitoring the operation of the patient support system 32. Such a system is further described in U.S. application Ser. No. 10/657,696, which was filed Sep. 8, 2003, is assigned to the assignees of the present application, and is expressly incorporated herein by reference. Alternatively or additionally, the network 100 can be based upon an alternative communication structure, for example, a peer-to-peer communication network, such as that disclosed by U.S. Pat. No. 5,771,511, which is assigned to the assignee of the present application and is expressly incorporated herein by reference.

Referring to FIG. 2A, the seven modules connected to network 100 in the illustrative embodiment of the patient support system 32 include a logic module 102, a communication module 104, a power supply module 106, a scale/PPM module 108, a dynamic surface module 110, a left caregiver control module 112, and a right control caregiver module 114.

Referring now to FIG. 2B, the various modules of network 100 are coupled to various sensors, actuators, and other components of the patient support system 32. For example, the scale/PPM module 108 is coupled to load cells 116 and a bed exit sensor 118. The scale/PPM module 108 and the logic module 102 are configured to detect, for example, a patient weight, position, and motion. Additionally, the modules 108 and 102 provide diagnostic information relating to the load cells 116, the bed exit sensor 118, and the scale/PPM module 108. The dynamic surface module 110 is configured to control, monitor, and provide diagnostic information relating to a mattress or other therapy surface of the patient support system 32. The dynamic surface module 110 is coupled to solenoids 124 or other valve actuators for controlling the characteristics of the mattress, and various sensors, for example, an angle position detector 120, a mattress sensor 122, and pressure transducers 126. The left caregiver control module 112 and the right caregiver control module 114 are each respectively coupled to left side rail controllers 128 and right side rail controllers 130. The caregiver control modules 112 and 114 and side rail controllers 128 and 130 provide control switch actuation and logic for controlling the patient support system 32 and provide diagnostic information relating to the various components of the modules 112 and 114 and the controllers 128 and 130.

Figure 2C:
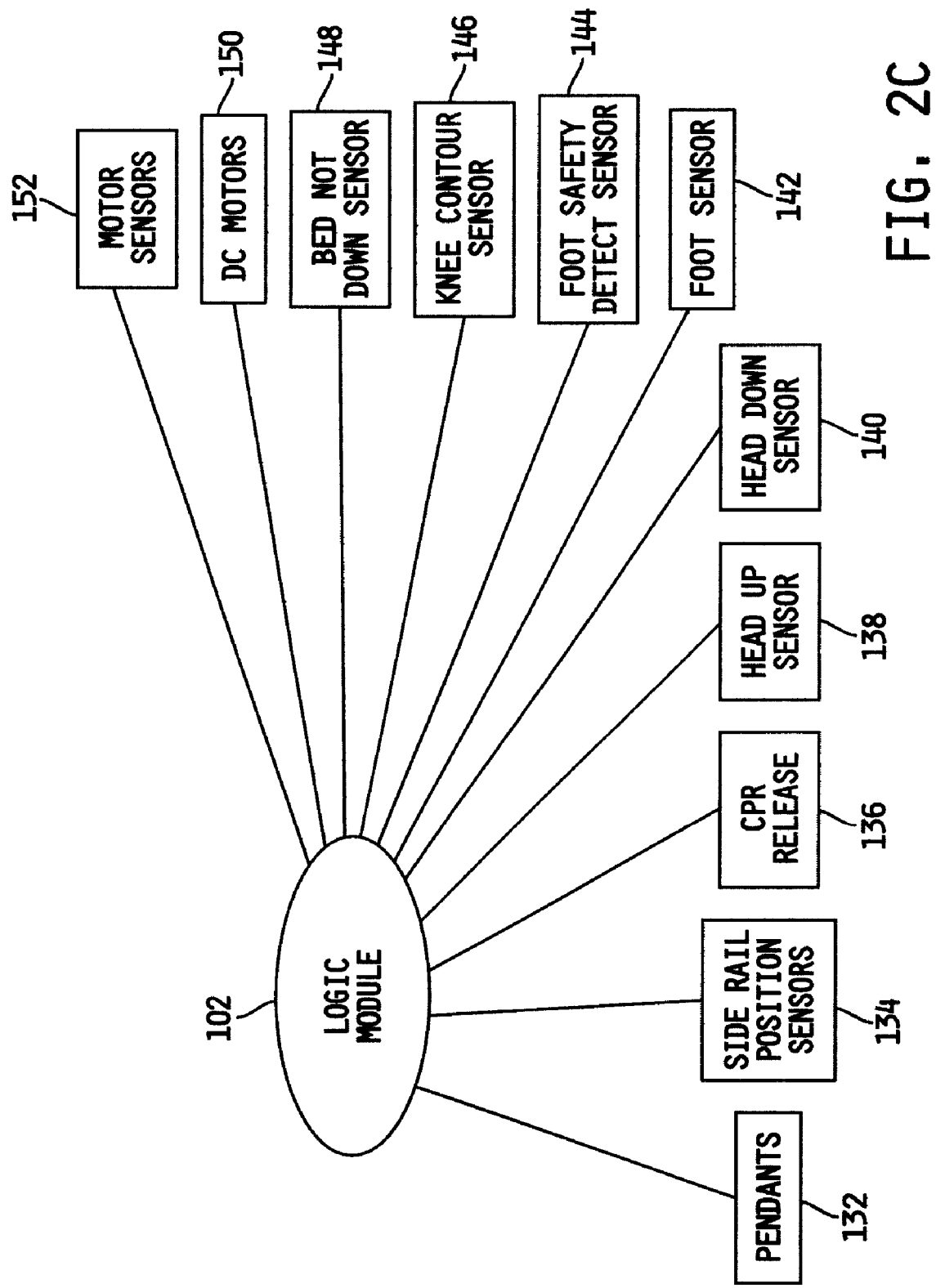

Referring to FIG. 2C, the logic module 102 is also coupled to a number of devices and sensors for which the logic module 102 is configured to provide diagnostic information. The devices and sensors include, for example, pendants 132, side rail position sensors 134, a CPR release switch 136, a head up sensor 138, a head down sensor 140, a foot position sensor 142, a foot safety detect sensor 144, a knee contour sensor 146, a bed not down sensor 148, DC Motors 150 and motor sensors 152. The motor sensors 152 can include electrical, mechanical, and temperature related sensors.

Figure 2D:
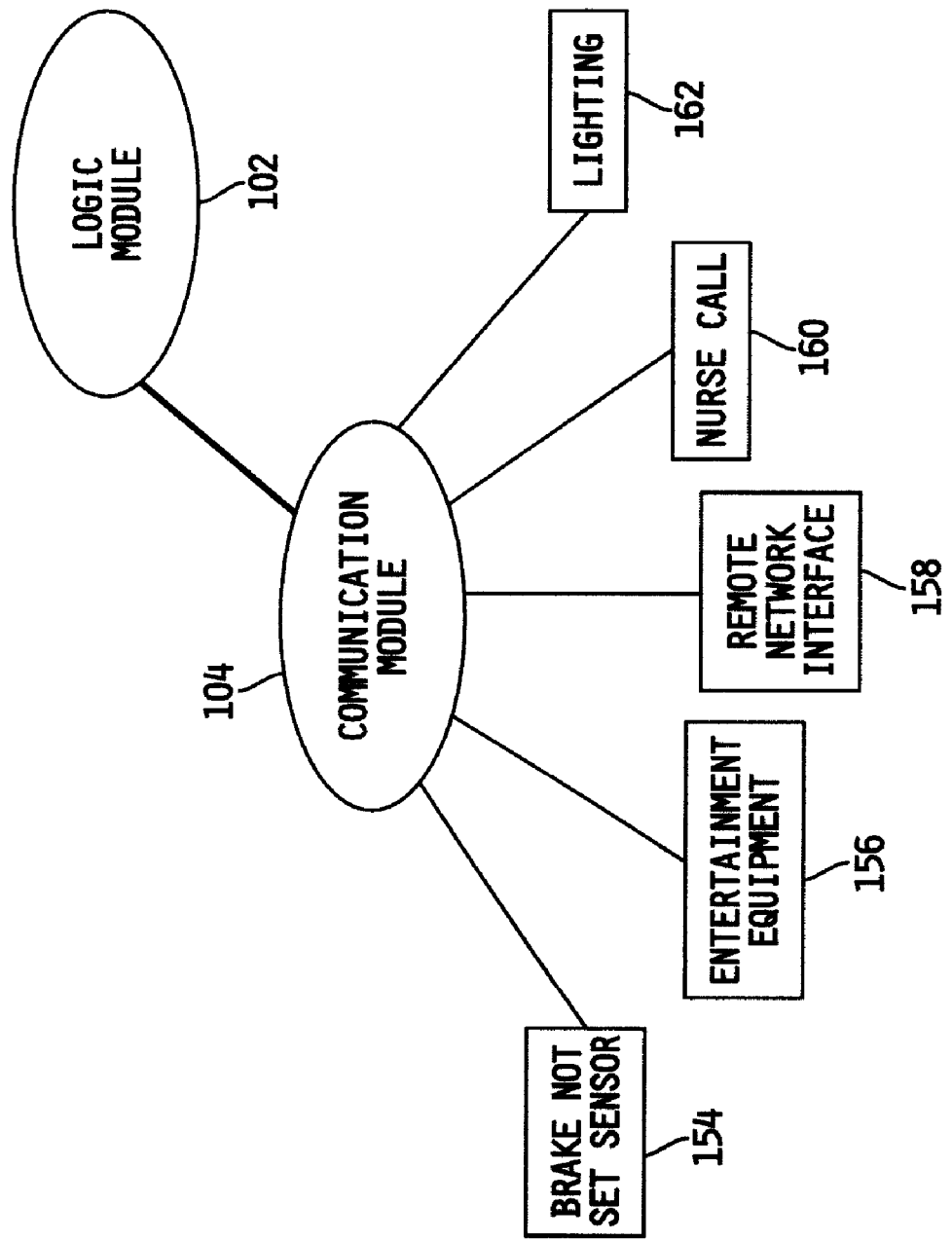

Referring to FIG. 2D, a communication module 104 is also coupled to the logic module 102. In the illustrative embodiment of FIG. 1, the bed communication device 46 is implemented in accordance with the communication module 104. The communication module 104 is coupled with a brake-not-set sensor 154, entertainment equipment 156, a network interface 158, a nurse call control 160, and room lighting controls 162. In the illustrative embodiment shown in FIG. 1, the communication interface 48 is implemented in accordance with the remote network interface 158. The communication module 104 not only detects diagnostic information relating to the devices shown in FIG. 2D, but is also configured to transmit diagnostic information relating to components of the patient support system 32 to which it is coupled or otherwise has data connectivity.

Figure 2E:
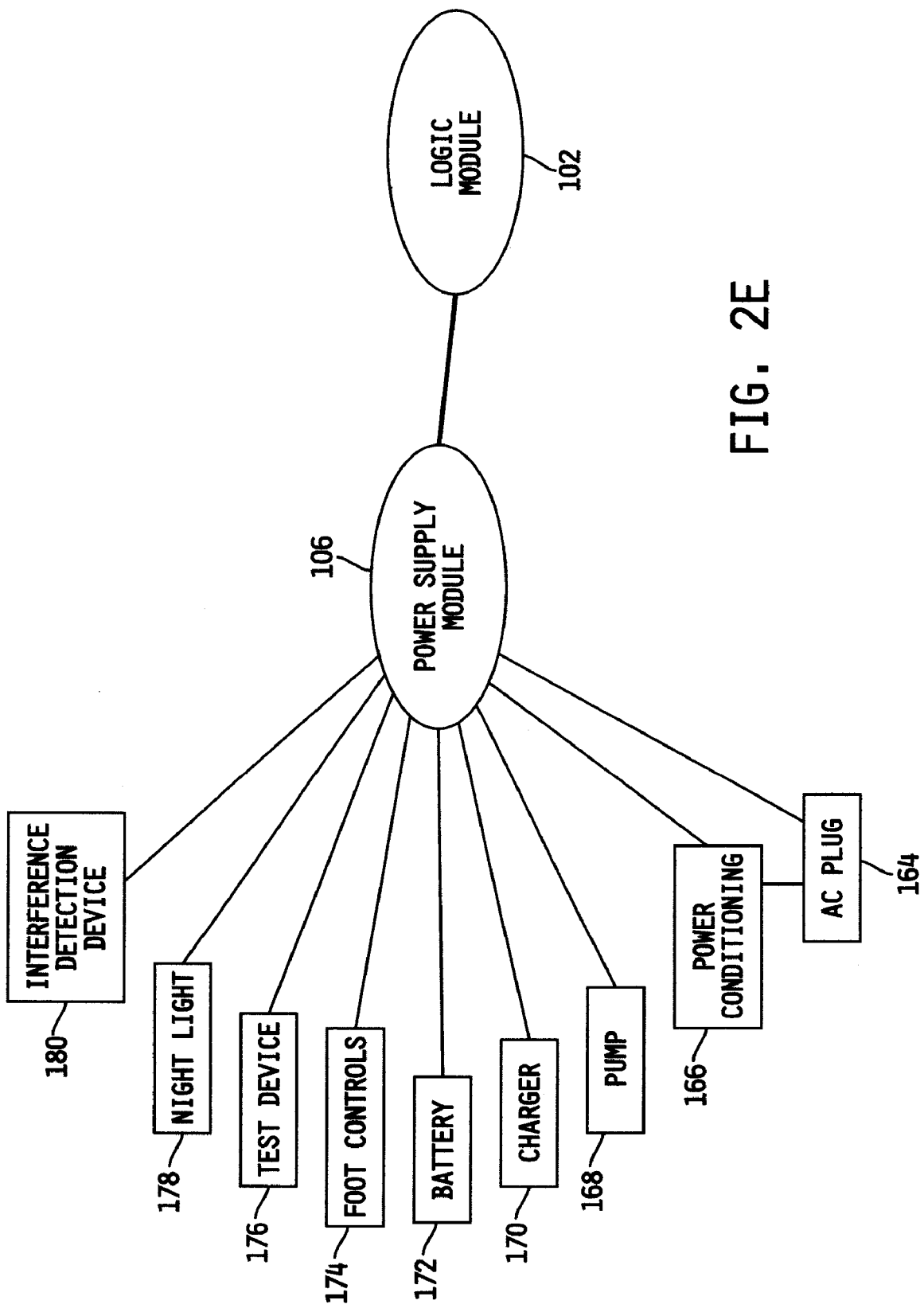

Referring to FIG. 2E, a power supply module 106 is also coupled to the logic module 102 and is configured to provide electrical power for, control and monitoring of, and provide diagnostic information regarding various devices to which it is coupled. Devices coupled to the power supply module 106 include, for example, an AC plug 164, power conditioning circuitry 166, a pneumatic or other pump 168, a battery charger 170, a battery 172, foot pedal controls 164, a testing device 176 for conducting various diagnostic and test functions, a night light 178, and an electrical/electromagnetic interference detection device 180.

The above described components associated with network 100 for which diagnostic information is provided to the monitoring device 38 are illustrative and not intended to be an all-inclusive list. Other components for which diagnostic information can be provided include, for example, drives, including motors, pumps, and actuators; user controls, including indicators and switches for the bed, lighting, entertainment, and nurse call; caregiver controls, including indicators and switches for bed positioning, drives, brakes, air systems, and other therapeutic systems; air systems, including compressors, blowers, bladders, and valves; movable members, including surfaces such as for the head, leg, knee, foot, elevation, and tilt, side rails, wheel systems, surface drive systems, braking systems, and linkages; power supplies, including battery voltage, charge state, charge current, discharge, and capacity; electronics, including control logic and communication circuits; load cells; and sensors for all of the above. The diagnostic information that is obtained and transmitted by the communication interface 48 can include or be related to vibration, displacement, rate, component temperature, ambient temperature, component humidity, ambient humidity, thermal loading, pressure, noise, mechanical load, current, voltage, electrical power, signal signature, calibration values, transit time, fault rate, logic or communication error, and accumulated usage, for example, the number of cycles or elapsed time compared to a predefined threshold.

Monitoring device 38 is configured to collect, monitor, and analyze the diagnostic information to predict and determine needed component replacement or service. Monitoring device 38 can be configured to compare diagnostic information to predefined thresholds and can additionally or alternatively use more complex analysis. For example, in order to identify and report preventative or responsive service requirements, the monitoring device 38 can use real-time and historical data, probabilistic methods, performance trends of an individual device and/or relative to other devices, and thresholds for diagnostic information. For example, monitoring device 38 can use remote diagnostic software, such as the SmartMonitor, TotalAccess, RemoteService (trademarks of Questra) and/or Service Agent software available from Questra of Redwood City, Calif. The software is configurable to provide remote Internet data and monitoring access as well as threshold and other diagnostic analysis of the received data in order to provide service alerts and other functions discussed herein. Alternatively, any or all of the collection, monitoring, analysis, identifying, and reporting operations of monitoring device 38 can be completed by other devices of monitoring system 30 configured for those operations, for example, sensor system 44, communication interface 48, bed server 75, or network application 78.

Figure 3:
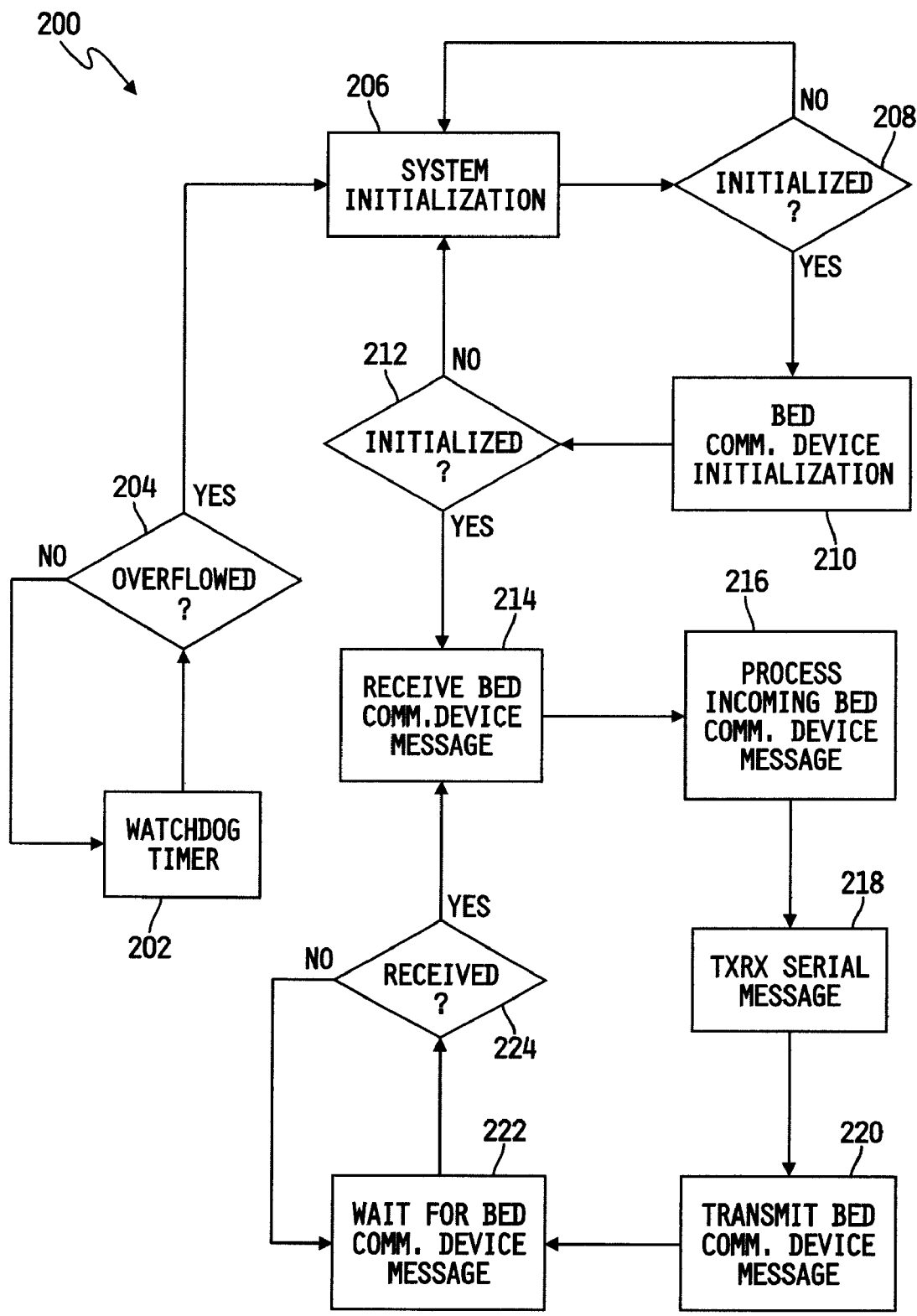
FIG. 3 is a flowchart of a software algorithm for a communication interface of the system of FIG. 1.

Referring now to FIG. 3, a flowchart shows one illustrative embodiment of a software algorithm or routine associated with the communications interface 48 and executed by the processor 50. The algorithm 200 begins at step 202. At step 202, the processor 50 initiates a watchdog timer providing a power on delay before the system initialization. At step 204, the processor 50 determines whether a preset limit for the watchdog timer has been exceeded. If so, then execution of the algorithm 200 continues at step 206, else execution returns to step 202. At step 206, the processor 50 initializes the hardware and/or software of the communication interface 48. At step 208, the processor 50 determines whether the communication interface 48 is initialized. If so, execution of the algorithm 200 continues at step 210, otherwise execution returns to step 206.

At step 210, the processor 50 initiates a signal to initialize the bed communication device 46. At step 212, the processor 50 determines whether the bed communication device 46 is initialized. If so, execution of the algorithm 200 continues at step 214, otherwise execution returns to step 206.

At step 214, the processor 50 receives any messages from the bed communication device 46. Note that according to this disclosure, the term message is used synonymous with the term data; however, the diagnostic information or other data is generally grouped into a set referred to as a message. At step 216, the processor 50 processes the incoming message from the bed communication device 46. Processing can include conversion from a message protocol used by the bed communication device to a different protocol.

At step 218, the processor 50 transmits the message in a converted protocol, for example, RS-232, to the network/webserver interface 54, 1054. At step 220, the processor 50 transmits available messages for the bed communication device 46. At step 222, the processor 50 looks for a message from the bed communication device 46. At step 224, the processor 50 determines whether a message is available for receipt from the bed communication device 46. If so, execution of the algorithm 200 returns to step 214, otherwise execution returns to step 222.

Figure 4:
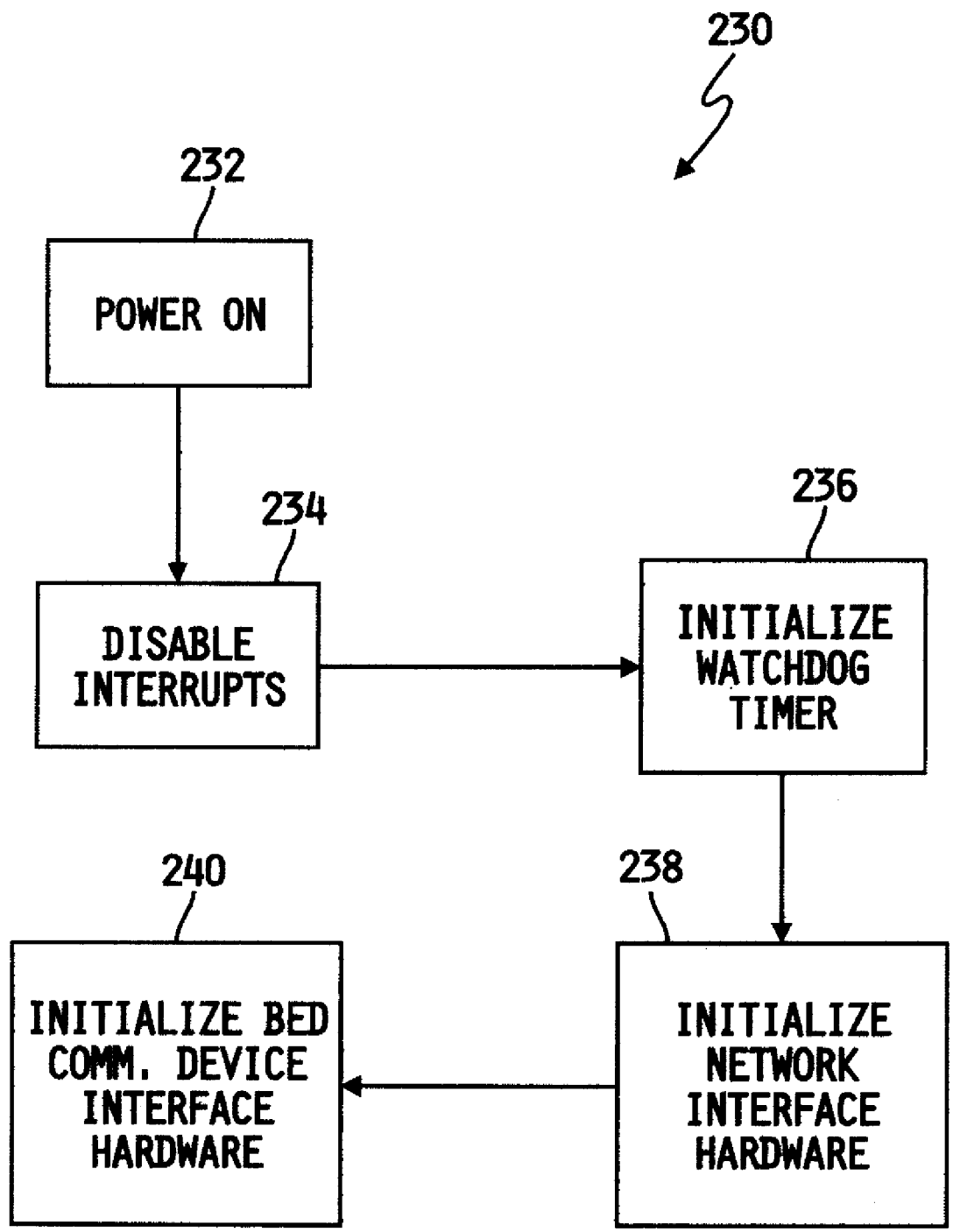
FIG. 4 is a flowchart of a software algorithm for initializing the communication interface of the system of FIG. 1.

Referring now to FIG. 4, a flowchart is shown of one illustrative embodiment of a software algorithm or routine for initializing the communication interface 48 of the monitoring system 30. Specifically, the algorithm 230 of FIG. 4 is called by and further describes step 206 of the algorithm 200 of FIG. 3. At step 232, power is provided to the communication interface 48. At step 234, the processor 50 disables interrupts, for example, those used for determining incoming communication data from the network/webserver interface 54, 1054 and the bed communication device 46.

At step 236, the processor 50 initializes the watchdog timer, providing a delay after power on and, for example, monitoring the hardware and/or software for a hang-up. At step 238, the processor 50 initializes the network/webserver interface hardware portion of the communication interface 48, which can be, for example, an optocoupler such as part number ILQ621 available from Vishay of Malvern, Pa. At step 240, the processor 50 initializes the bed communication device interface hardware portion of the communication interface 48, which can be, for example, a multichannel RS-232 driver/receiver such as part number MAX232 available from Maxim Integrated Products of Sunnyvale, Calif.

Figure 5:
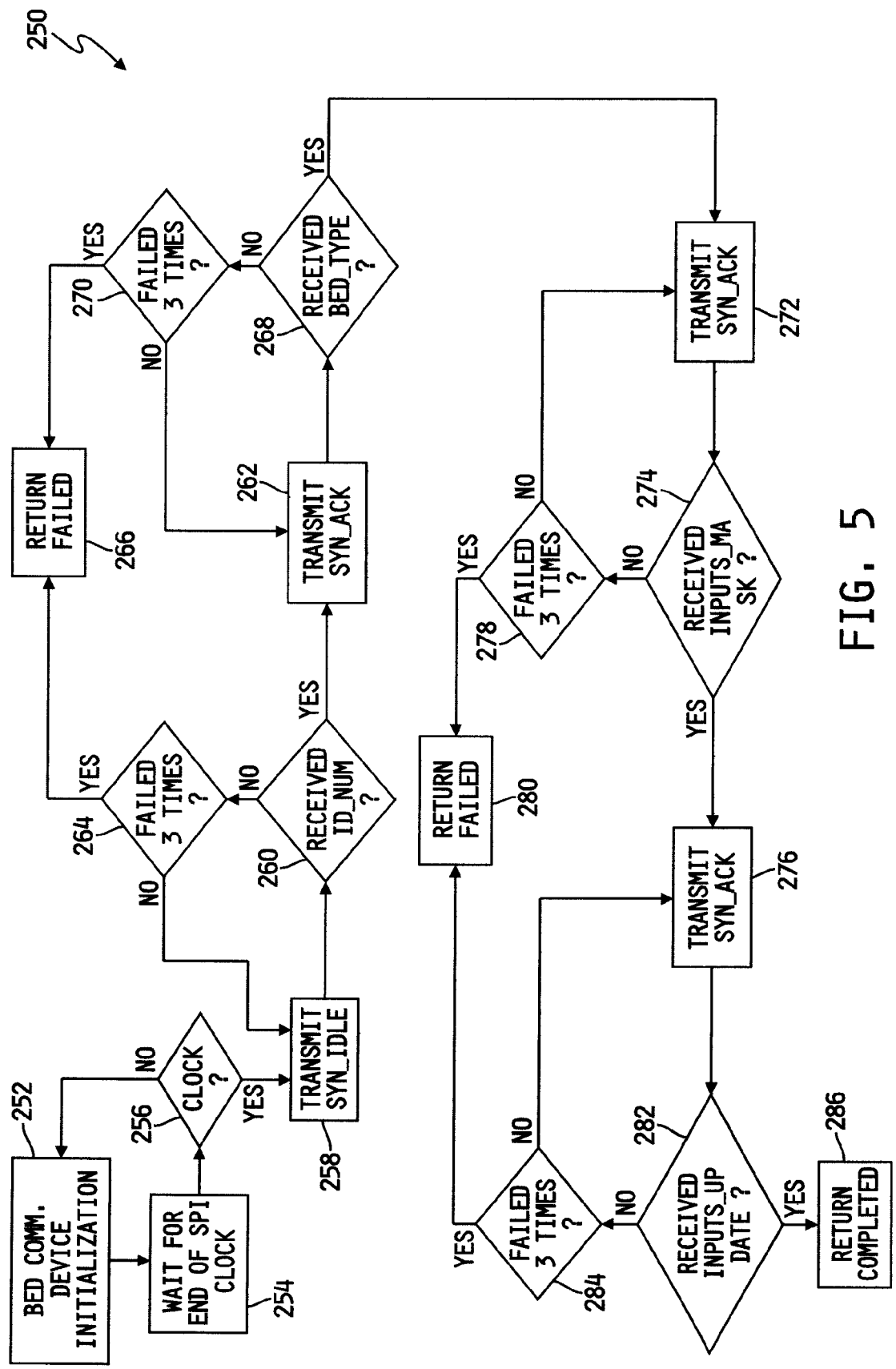
FIG. 5 is a flowchart of a software algorithm associated with the communication interface of the system of FIG. 1 and for initializing communication with the patient support system.

Referring now to FIG. 5, a flowchart is shown of one illustrative embodiment of a software algorithm or routine for the communication interface 48 initializing the bed communication device 46 of the monitoring system 30. Specifically, the algorithm 250 of FIG. 5 is called by step 240 of the algorithm 230 as shown in FIG. 4. The algorithm 250 begins at step 252. At step 252, processor 50 sends a signal or data to the bed communication device 46 to initialize communication between the communication interface 48 and the bed communication device 46. At step 254, the processor 50 waits for the end of an SPI clock signal. At step 256, processor 50 determines whether the SPI clock is present. If not, initialization of the bed communication device 46 has not begun and execution of the algorithm 250 returns to step 252. If the processor 50 determines the clock signal is present, execution of the algorithm 250 continues at step 258.

At step 258, the processor 50 transmits a SYN_IDLE message to the bed communication device 46 to begin polling the bed communication device 46 for data relating to the patient support system 32. At step 260, the processor 50 determines whether a ID_NUM message is received from the bed communication device 46. If so, execution of the algorithm 250 continues at step 262, else, execution continues at step 264. If execution continues at step 264, the processor 50 determines whether the ID_NUM message has failed to be received three times. If so, at step 266, execution of the algorithm is complete and returns to step 240 of the calling algorithm 230. If not, execution of the algorithm 250 returns to step 258 to reinitiate the communication.

At step 262, the processor 50 transmits a SYN_ACK message to the bed communication device 46, acknowledging successful communication with the device 46. At step 268, the processor 50 determines whether a BED_TYPE message is received from the bed communication device 46. If so, execution of the algorithm 250 continues at step 272, else execution continues at step 270. If execution continues at step 270, processor 50 determines whether failure to receive the BED_TYPE message has occurred three times. If so, execution of the algorithm 250 continues at step 266, else execution returns to step 262.

At step 272, the processor 50 transmits a SYN_ACK message to the bed communication device 46, acknowledging receipt of the BED_TYPE message. At step 274, the processor 50 determines whether an INPUTS_MASK message has been received from the bed communication device 46. If so, execution of the algorithm 250 continues at step 276, else execution continues at step 278. If execution continues at step 278, the processor 50 determines whether receipt of the INPUTS_MASK message has failed three times. If so, execution of the algorithm 250 continues at step 280, else execution returns to step 272. At step 280, execution of the algorithm 250 is complete and returns to the calling step 240 of the algorithm 230 of FIG. 4.

At step 276, the processor 50 transmits a SYN_ACK message to the bed communication device 46, acknowledging receipt of the INPUTS_MASK message. At step 282, the processor 50, determines whether a INPUTS_UPDATE message has been received from the bed communication device 46. If so, execution of the algorithm 250 continues at step 286, else execution continues at step 284. If step 284 is completed, the processor 50 determines whether receipt of the INPUTS_UPDATE message has failed three times. If so, execution of the algorithm 250 continues at step 280, else execution returns to step 276. At step 286, the algorithm 250 is complete and execution returns to calling step 240 of the algorithm 230 in FIG. 4.

The INPUTS_MASK message includes data relating to the accessories and/or options associated with the patient support system 32. The INPUTS_UPDATE message includes data relating to the current state of the patient support system 32, for example, as detected by sensors or other components associated with the sensor system 44.

Figure 6A:
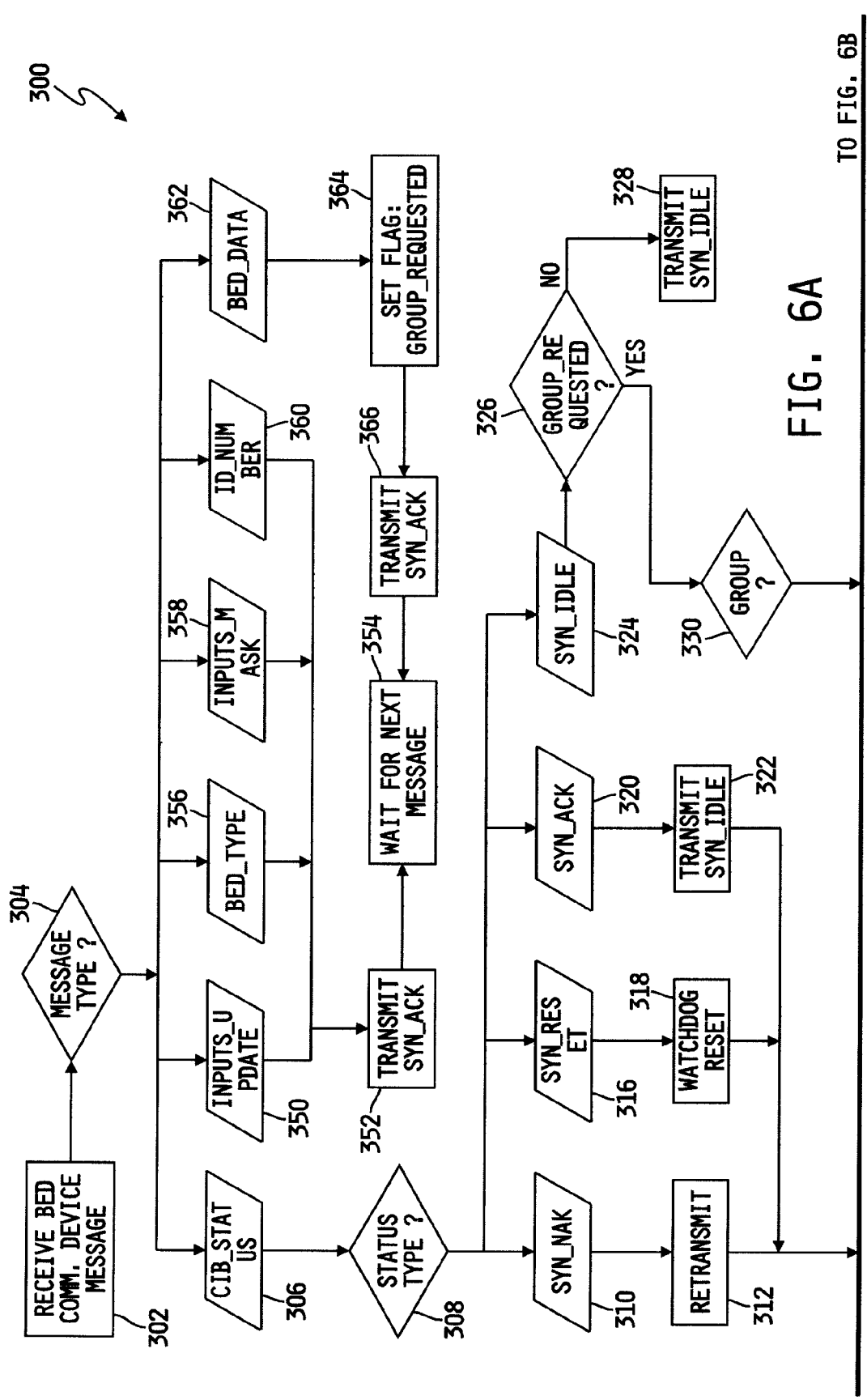
FIGS. 6A and 6B are a flowchart of an illustrative software algorithm associated with the communication interface of the system of FIG. 1 and for providing communication between the patient support system and the communication interface.
Figure 6B:
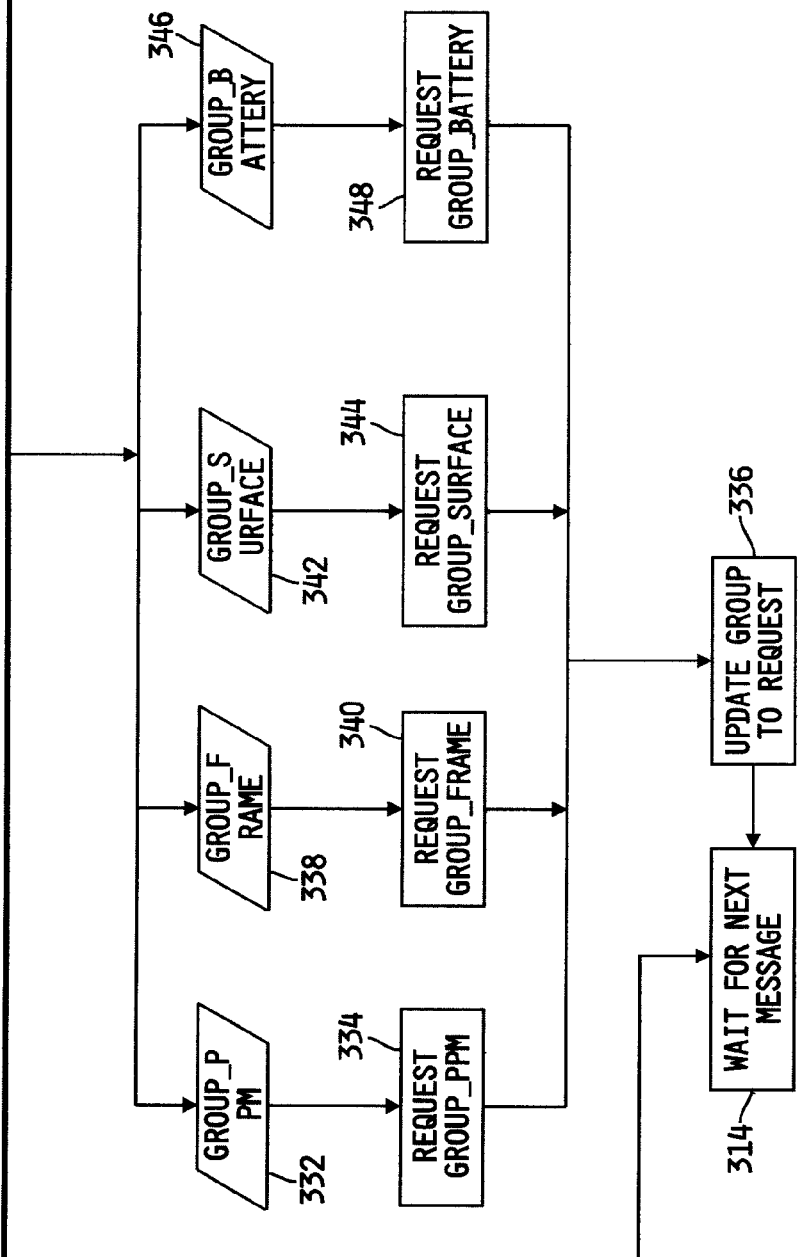

Referring now to FIGS. 6A and 6B, a flowchart is shown of one illustrative embodiment of a software algorithm or routine for handling communication between the bed communication device 46 and the communication interface 48. Specifically, algorithm 300 associated with the communication interface 48 expands upon and is called by steps 214-224 of the algorithm 200, as shown in FIG. 3.

At step 302, processor 50 receives a message from the bed communication device 46. At step 304, the processor 50 determines the type of message received. After execution of step 304, the algorithm 300 continues at one of steps 306, 350, 356, 358, 360, and 362, depending on the message type received. At step 306, a CIB_STATUS message is received, which is an acknowledgment message from the bed communication device 46. At step 308, processor 50 determines the type of acknowledgment status received. After step 308, execution of the algorithm 300 continues at one of step 310, 316, 320, and 324, depending on the acknowledgment status type received.

At step 310, the status type received by processor 50 is SYN_NAK message, which indicates the bed communication device 46 failed to receive a message transmitted by the communication interface 48. At step 312, processor 50 retransmits the message to the bed communication device 46. At step 314, the processor 50 waits for the next message received from the bed communication device 46.

At step 316, the processor 50 receives a status type SYN_RESET message indicating the bed communication device 46 has requested a reset of communication. At step 318, the processor 50 resets the watchdog timer to reinitialize the communication between the communication interface 48, and the bed communication device 46. After step 318, execution of the algorithm 300 continues at step 314.

At step 320, the processor 50 receives a status type SYN_ACK message from the bed communication device 46 indicating the device 46 successfully received the message transmitted by the communication interface 48. At step 322, the processor 50 transmits a SYN_IDLE message. After step 322, execution of the algorithm 300 continues at step 314.

At step 324, the processor 50 receives a status type SYN_IDLE message from the bed communication device 46. The SYN_IDLE message indicates that communication is still established but no other status type or message has been transmitted by the device 46. At step 326, the processor 50 determines whether a bed data GROUP_REQUEST message is to be requested, for example, if received from the network/webserver interface 54, 1054, or periodically requested by the processor 50. If a GROUP_REQUEST message has been received, then execution of the algorithm 300 continues at step 330, otherwise step 328 is executed. At step 328, the processor 50 acknowledges the SYN_IDLE message to the bed communication device 46 and transmits the SYN_IDLE message to the network/webserver interface 54, 1054. After step 328, execution of the algorithm 300 continues at step 314.

At step 330, the processor 50 determines which GROUP_REQUEST message has been received, resulting in one of steps 332, 338, 342, and 346 being executed next. If a GROUP_PPM bed data message is requested, then at steps 332 and 334, processor 50 transmits a REQUEST_GROUP_PPM message in the proper protocol to the bed communication device 46. If a GROUP_FRAME bed data message is requested, then at steps 338 and 340, processor 50 transmits a REQUEST_GROUP_FRAME message in the proper protocol to the bed communication device 46. If a GROUP_SURFACE bed data message is requested, then at steps 342 and 344, processor 50 transmits a REQUEST_GROUP_SURFACE message in the proper protocol to the bed communication device 46. If a GROUP_BATTERY bed data message is received, then at steps 346 and 348, processor 50 transmits a REQUEST_GROUP_BATTERY message in the proper protocol to the bed communication device 46.

After step 334, 340, 344, or 348 is completed, the algorithm 300 continues at step 336. At step 336, the processor 50 acknowledges the group that was requested and indexes to the next group to request, or awaits the next group request message received from the network/webserver interface 54, 1054. At step 314, the processor 50 waits for the next message received from the bed communication device 46.

At step 350, the message type received by the processor 50 is INPUTS_UPDATE, which indicates that a state of the data associated with the patient support system 32 and transmitted by the bed communication device 46 has changed and is therefore being broadcast by the device 46. At step 352, the processor 50 transmits a SYN_ACK message to the bed communication device 46. At step 354, the processor 50 waits for the next message to be received from the bed communication device 46.

At step 356, the message type received by the processor 50 is BED_TYPE. After step 356 is completed, execution of the algorithm continues at step 352. At step 358, the message type received by the processor 50 is INPUTS_MASK, which indicates the accessories and/or options associated with the patient support system 32. After step 358 is completed, execution of the algorithm continues at step 352.

At step 360, the message type received by the processor 50 is ID_NUMBER. After step 360 is completed, execution of the algorithm continues at step 352.

At step 362, the processor 50 receives the message type BED_DATA, which is a message from the bed communication device 46 responding to a specific request for data. At step 364, the processor 50 sets a data flag GROUP_REQUESTED indicating that a message containing the earlier requested data has been received. At step 366, the processor 50 transmits a SYN_ACK message to the bed communication device 46. At step 354, the processor 50 waits for the next message to be received from the bed communication device 46.

Figure 7:
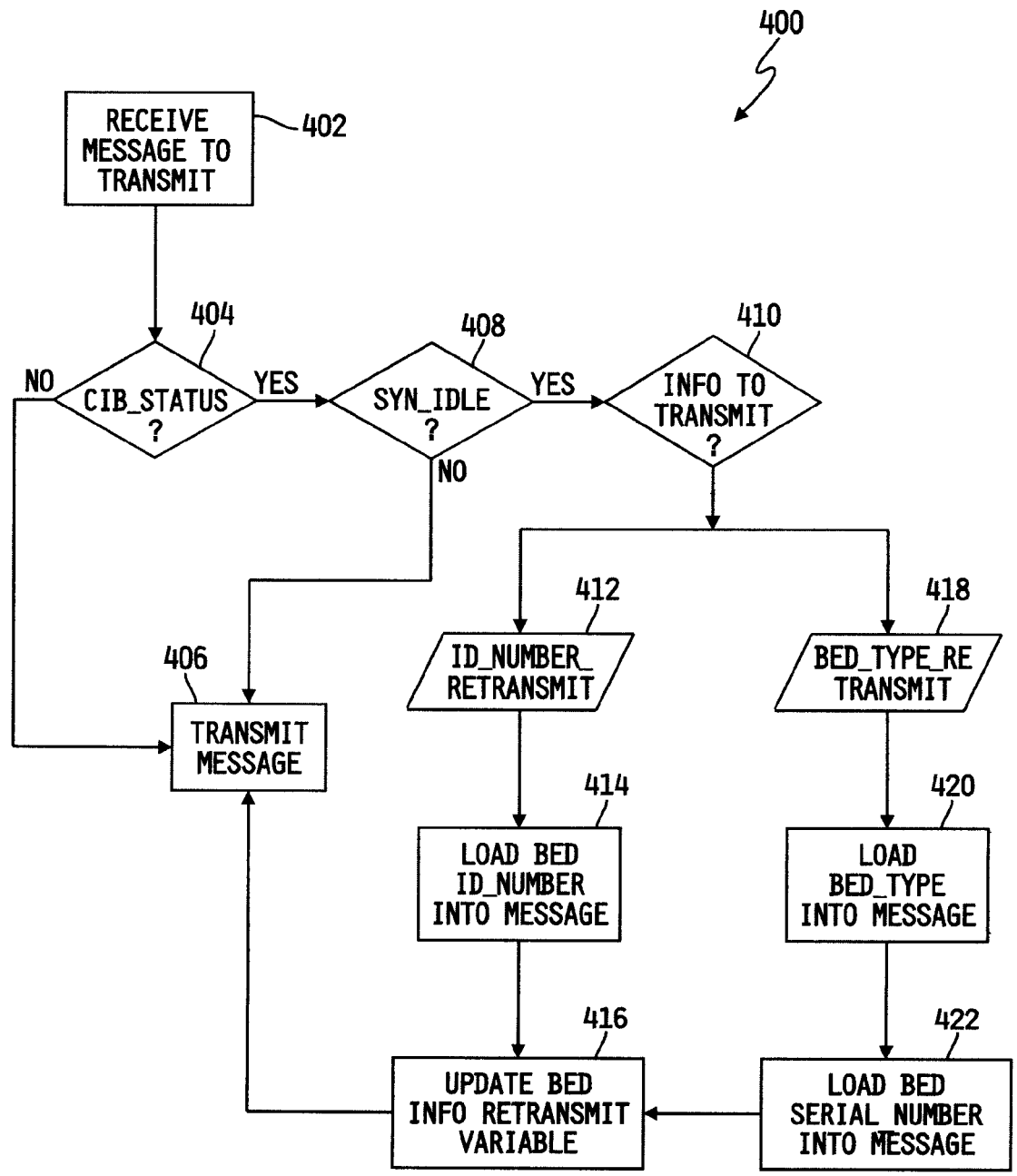
FIG. 7 is a flowchart of a software algorithm associated with the communication interface of the system of FIG. 1 and for providing communication between the communication interface and network or web server interface.

Referring now to FIG. 7, a flowchart is shown for one illustrative embodiment of a software algorithm or routine for handling communication between the communication interface 48 and the network/webserver interface 54, 1054. Specifically, algorithm 400 is called by and expands upon step 218 of the algorithm 200 shown in FIG. 3, and is executed by processor 50 of the communication interface 48.

At step 402, the processor 50 prepares, for example, converting protocol if required, a message received from bed communication device 46 for transmission to the network/webserver interface 54, 1054. At step 404, the processor 50 determines whether a CIB_STATUS message is included in the message received from the bed communication device 46. A CIB_STATUS message is a message giving status information relating to bed communication device 46. If so, then step 408 is executed, else, step 406 transmits the converted message to the network/webserver interface 54, 1054.

If step 408 is executed, then the processor 50 determines whether the message received from the bed communication device 46 includes a SYN_IDLE message, indicating no other data is presently available for transmission. If so, step 410 is executed, else step 406 is executed. At step 410, the processor 50 determines whether the bed info retransmit variable indicates there is bed information data that has been earlier stored in communication interface 48 for later transmission after communication is established and during a SYN_IDLE time of the bed communication device 46. If so, then steps 412 and 418 are executed as determined by the contents of the bed info retransmit variable, else execution of algorithm 400 returns to step 218 of the algorithm 200.

At step 412, the processor 50 obtains the BED_ID_NUMBER from an associated memory device. At step 414, the processor 50 loads the BED_ID_NUMBER into the message to be transmitted. At step 418, the processor 50 obtains the BED_TYPE from an associated memory device. At step 420, the processor 50 loads the BED_TYPE into the message to be transmitted. At step 416, the processor 50 updates the bed information retransmit variable to indicated the bed information has been loaded into a message and transmitted. After step 416 is executed, the assembled messaged is transmitted to the network/webserver interface 54, 1054 at step 406. After execution of step 406, the algorithm 400 is complete and execution returns to step 218 of the algorithm 200.

Figure 8:
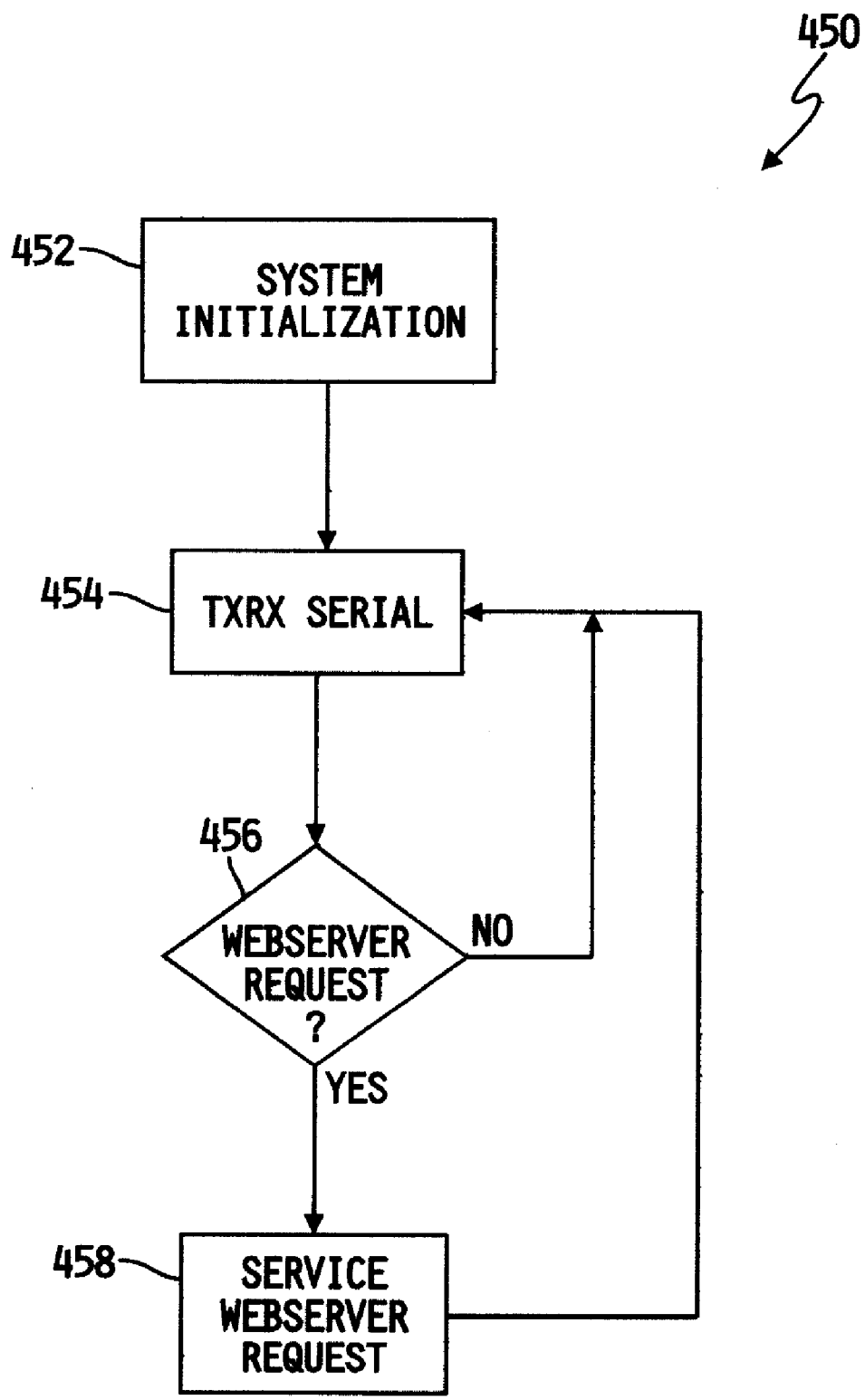
FIG. 8 is a flowchart of a software algorithm associated with the webserver interface of the system of FIG. 1.

Referring now to FIG. 8, a flowchart is shown of one illustrative embodiment of a software algorithm representing the overview of the software algorithm associated with the webserver 54 of the monitoring system 30. Specifically, algorithm 450 begins at step 452. At step 452, processor 56 of the webserver 54 initializes the software and/or hardware of the webserver 54. At step 454, the processor 56 transmits and/or receives communication with the communication interface 48. At step 456, the processor 56 determines whether a request has been presented to the webserver 54. If so, step 458 is executed, otherwise execution of the algorithm 450 returns to step 454. At step 458, the processor 56 services the request received by the webserver 54, for example, incorporating new data from the patient support system 32 into the webpages assembled by webserver 54.

Figure 9:
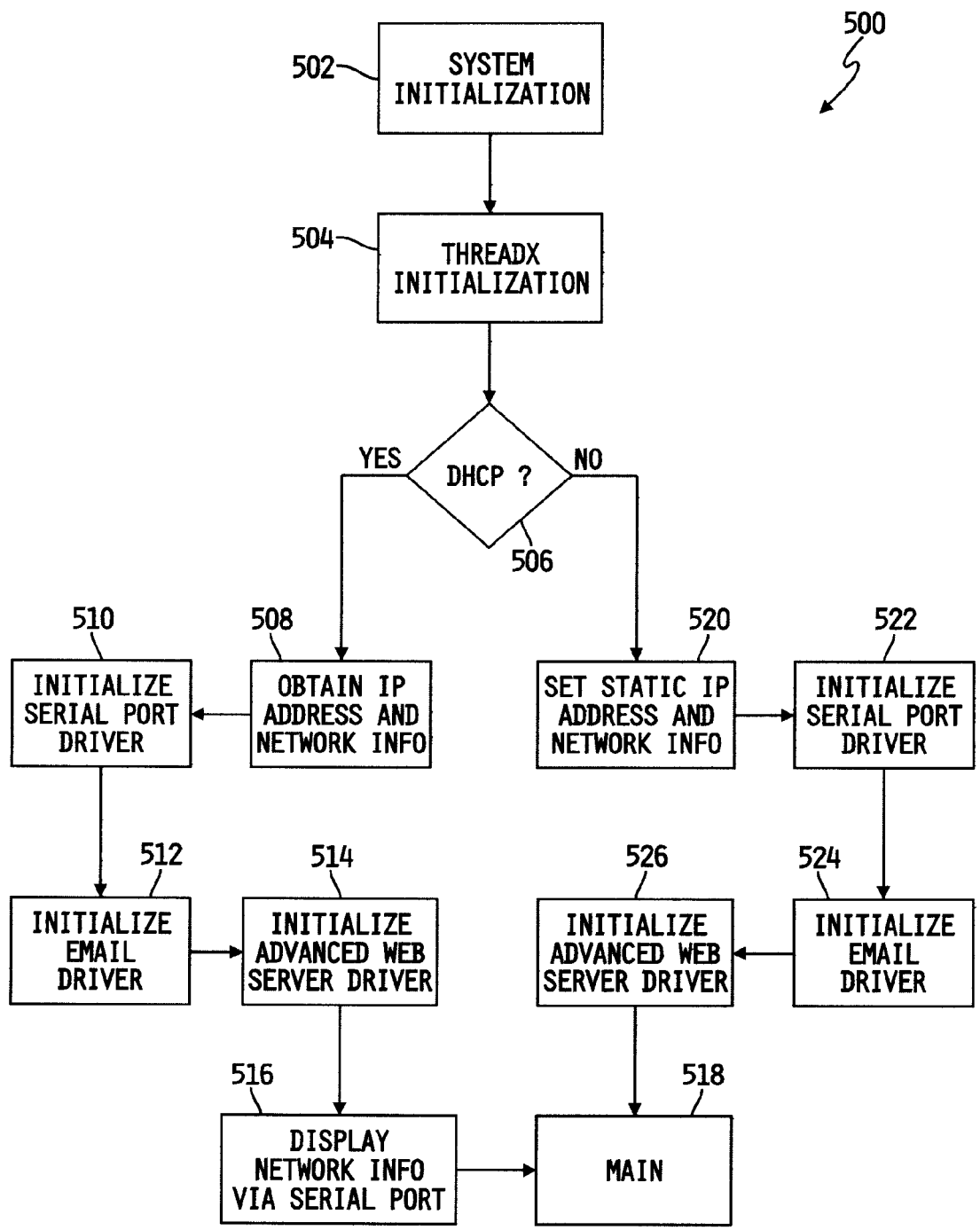
FIG. 9 is a flowchart of a software algorithm associated with the webserver interface of the system of FIG. 1 and for initializing the webserver interface.

Referring now to FIG. 9, a flowchart is shown for one illustrative embodiment of a software algorithm for initializing the hardware and/or software of the webserver 54. Specifically, an algorithm 500 shown in FIG. 9 expands upon and is called by step 452 of the algorithm 450 shown in FIG. 8. The algorithm 500 begins at step 502. At step 504, processor 56 initializes the Thread X™ (Thread X is a trademark of Express Logic, Inc. of San Diego, Calif.), an embedded real time operating system associated with the webserver 54.

At step 506, the processor 56 determines whether a dynamic host configuration protocol (DHCP) has been selected. If so, then step 508 is executed, else execution of the algorithm 500 continues at step 520. At step 508, the processor 56 obtains the dynamic internet protocol (IP) address and network information. At step 510, the processor 56 initializes the communication port coupling the webserver 54 and communication interface 48 via datalink 58, for example, an RS-232 connection. At step 512, the processor 56 initializes an e-mail driver associated with the webserver 54. At step 514, the processor 56 initializes an advanced webserver driver associated with the webserver 54. At step 516, the processor 56 displays the network information via the communication port associated with datalink 58. At step 518, the algorithm 500 is complete and execution returns to step 452 of the algorithm 450 shown in FIG. 8.

If at step 506, it is determined that DHCP is not selected, then at step 520, processor 56 sets a static IP address and network information. At step 522, the processor 56 initializes the communication port associated with datalink 58 and coupling the webserver 54 and the communication interface 48. At step 524, the processor 56 initializes the e-mail driver associated with the webserver 54. At step 526, the processor 56 initializes the advanced webserver driver associated with the webserver 54. At step 518, execution of the algorithm 500 is complete and returns to step 452 of the algorithm 450 shown in FIG. 8.

Figure 10A:
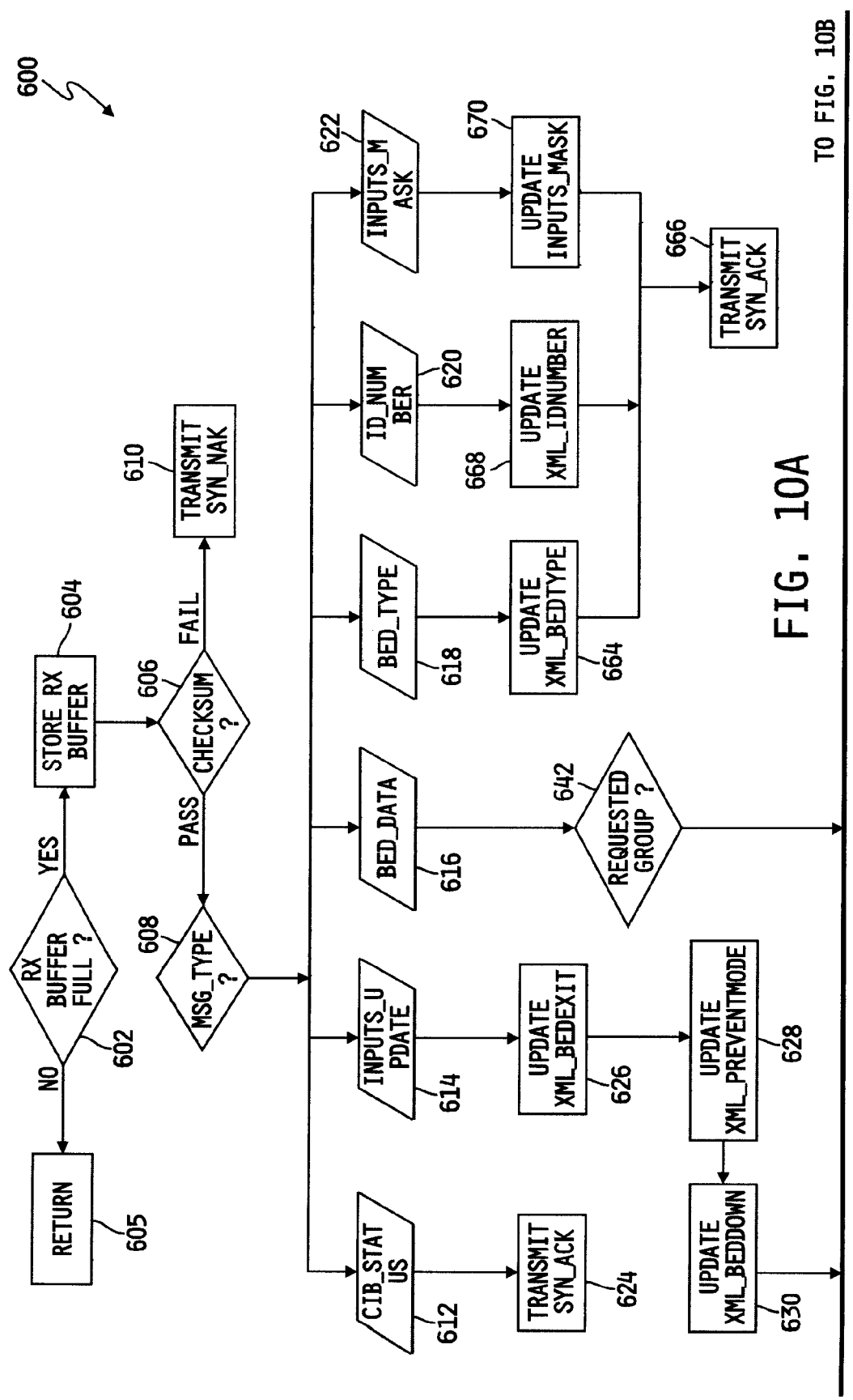
FIGS. 10A and 10B are a flowchart of a software algorithm associated with the network interface of the system of FIG. 1 and for providing communication between the communication interface and the webserver interface.
Figure 10B:
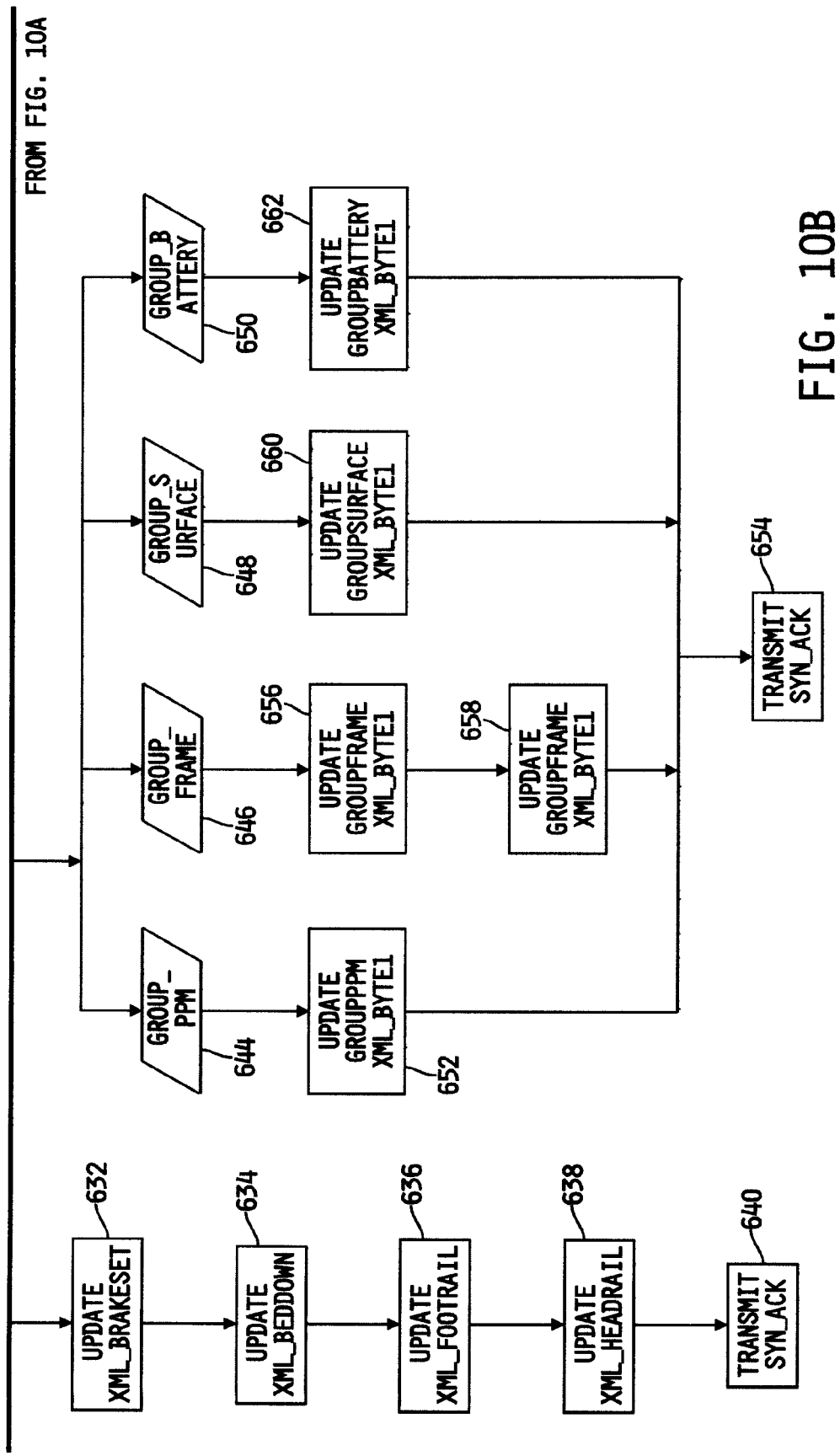

Referring now to FIG. 10, a flowchart is shown of one illustrative embodiment of a software algorithm for the webserver 54 handling communication between the communication interface 48 and the webserver 54. Specifically, an algorithm 600 is called by and expands upon step 454 of the algorithm 450 shown in FIG. 8. At step 602, the processor 56 determines whether the received buffer is full. If so, execution of the algorithm 600 continues at step 604, else step 605 is completed. At step 605, the algorithm 600 is complete and execution returns to the calling step 454 of the algorithm 450 and FIG. 8.

At step 604, the processor 56 stores the received buffer. At step 606, the processor 56 determines whether the checksum of the received buffer passes or fails. If the checksum passes, execution of the algorithm 600 continues at step 608, else execution continues at step 610. In the event of a checksum failure, at step 610, the processor 56 transmits a SYN_NAK message to the communication interface 48, indicating a communication error. After execution of step 610, the algorithm 600 is complete and execution returns to the calling step 454 of the algorithm 450 and FIG. 8.

At step 608, the processor 56 determines the message type received by the webserver 54. Depending upon the message type received, execution of the algorithm 600 continues at one of steps 612, 614, 616, 618, 620, and 622. At step 612, the message type received is CIB_STATUS, a message indicating the status of bed communication device 46. At step 624, processor 56 transmits a SYN_ACK message to the communication interface 48.

If at step 608, the processor 53 determines that the message type received is INPUTS_UPDATE, then step 614 is executed. In step 626, the processor 56 updates the extensible markup language (XML) variable xml_bedexit from the message received from the communication interface 48. At step 628, the processor 56 updates the xml_preventmode variable.

At step 630, the processor 56 updates the xml_beddown variable. At step 632, the processor 56 updates the xml_brakeset variable. At step 634, the processor 56 updates the xml_beddown variable. At step 636, the processor 56 updates the xml_footrail variable. At step 638, the processor 56 updates the xml_headrail variable. At step 640, the processor 56 transmits a SYN_ACK message to the communication interface 48. After executing step 640, the algorithm 600 is complete and execution returns to the calling step 454 of the algorithm 450 and FIG. 8

If at step 608 the processor 56 determines that the message type is BED_DATA, then step 616 is executed. At step 642, the processor 56 determines what group data is requested from the patient support system 32. Depending on the group requested, execution of the algorithm 600 continues at one of steps 644, 646, 648, and 650.

At step 644, the GROUP_PPM datagroup is requested. At step 652, the processor 56 updates the groupPPMxml_byte1 variable. At step 654, the processor 56 transmits SYN_ACK message to the communication interface 48. After execution of step 654, the algorithm 600 is complete and execution returns to the calling step 454 of the algorithm 450 and FIG. 8

If at step 642, the processor 56 determines that the request is for GROUP_FRAME, then step 646 is executed. At step 656, the processor 56 updates the groupFramexmlbyte1 variable. At step 658, the processor 56 updates the groupFramexmlbyte2. After step 658 is completed, execution of the algorithm 600 continues at step 654.

If at step 642 it is determined that the requested group is GROUP_SURFACE, then step 648 is executed. At step 660, the processor 56 updates the groupSurfacexml_byte1 variable. After step 660 is complete, execution of the algorithm 600 continues at step 654.

If at step 642, the processor 56 determines that the group requested is GROUP_BATTERY, then step 650 is completed. At step 662, the processor 56 updates the groupBatteryxml_byte1. After step 662 is completed, execution of the algorithm 600 continues at step 654.

If at step 608, the processor 62 determines that the message type is BED_TYPE, then step 618 is completed. At step 664, the processor 56 updates the xml_bedtype variable. At step 666, the processor 56 transmits a SYN_ACK message to the communication interface 48.

If at step 608 the message type is determined to be ID_NUMBER, then step 620 is completed. At step 668, the processor 56 updates the xml_IDNUMBER variable. After step 668 is completed, execution of the algorithm 600 continues at step 666.

If at step 608, the message type is determined to be INPUTS_MASK, then step 622 is completed. At step 670, the processor 56 updates the inputs_mask variable. After step 670 is completed, execution of the algorithm 600 continues at step 666.

Figure 11B:
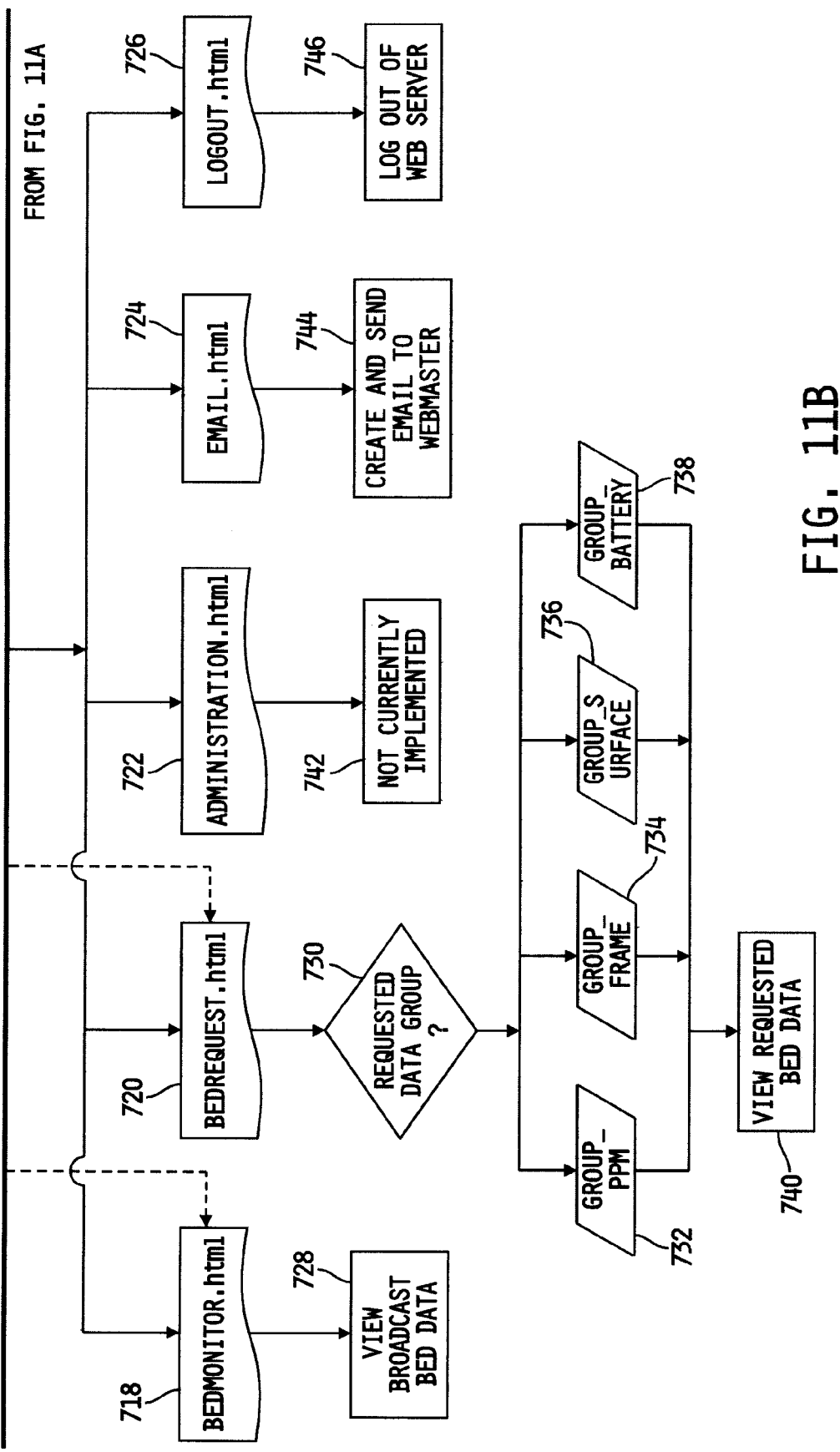

Referring now to FIGS. 11A and 11B, a flowchart is shown for one illustrative embodiment of a software algorithm or routine for webpage processing by the webserver 54. Specifically, an algorithm 700 is called by and expands upon the steps 456 and 458 of the algorithm 450 shown in FIG. 8.

Figure 16A:
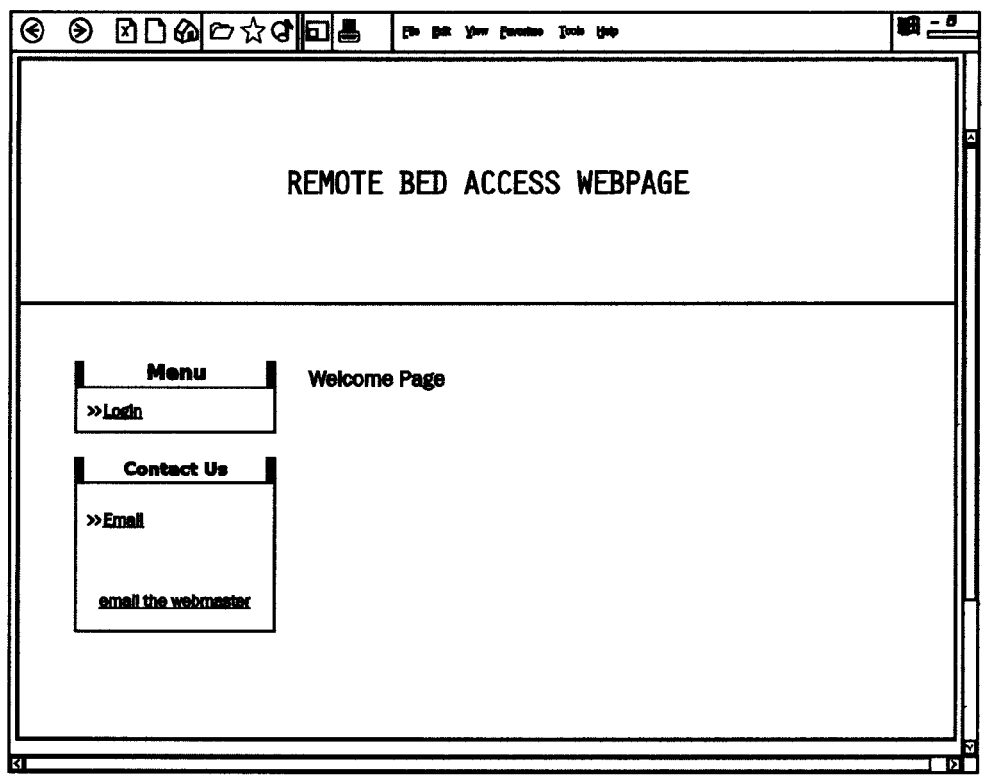
FIG. 16A is a screen shot of a home webpage associated with the webserver interface of the system of FIG. 1.
Figure 16B:
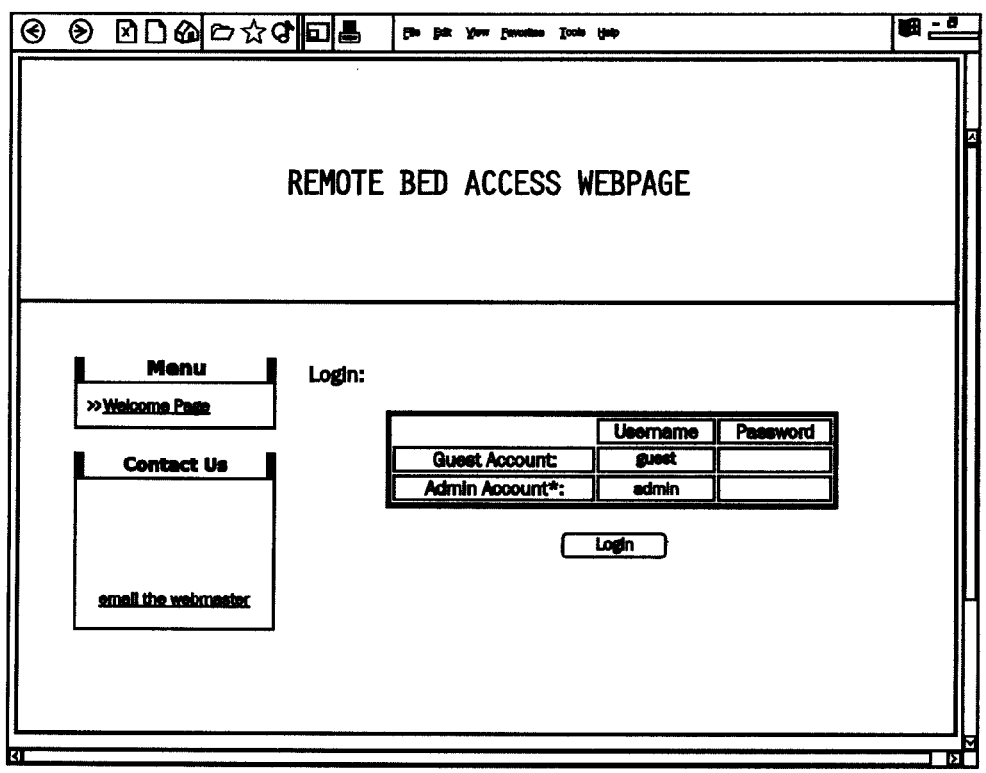
FIG. 16B is a screen shot of a login webpage associated with the webserver interface of the system of FIG. 1.

At step 702, the processor 56 provides a welcome webpage, such as that shown in the plan form of FIG. 16A. At step 704, the processor 56 provides a login webpage, such as that shown in the screen shot of FIG. 16B. At step 706, the processor 56 determines whether a correct ID and password have been entered. If so, execution of the algorithm 700 continues at step 708, else step 710 is executed. At step 710, processor 56 provides an access error to the requested user.

Figure 16C:
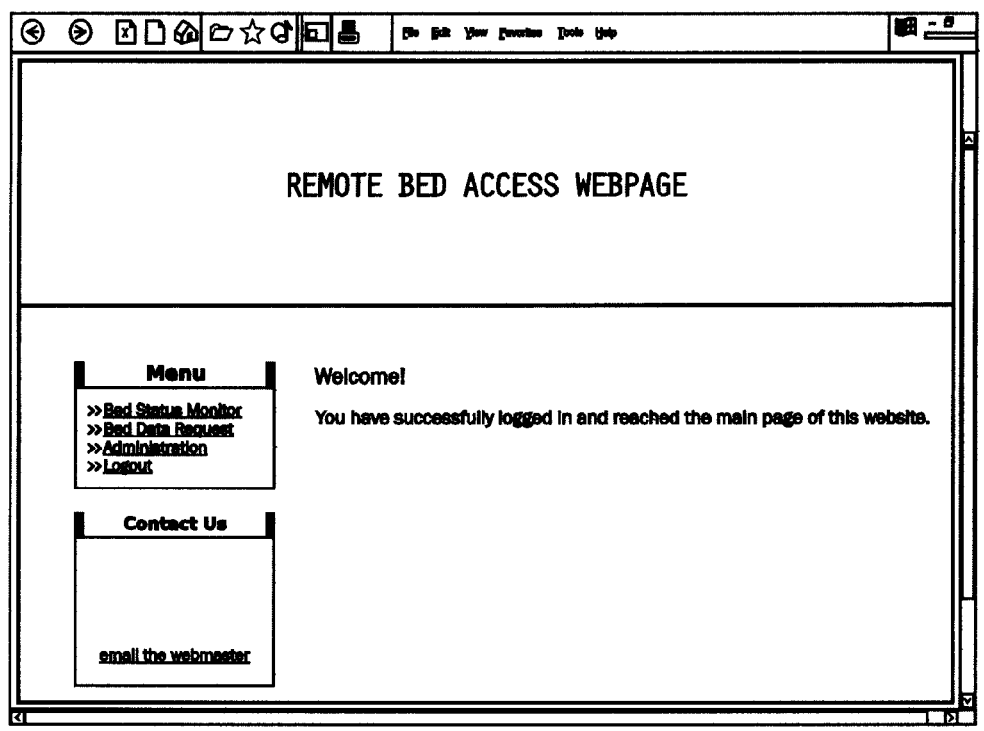
FIG. 16C is a screen shot of a logged in webpage associated with the webserver interface of the system of FIG. 1.
Figure 16D:
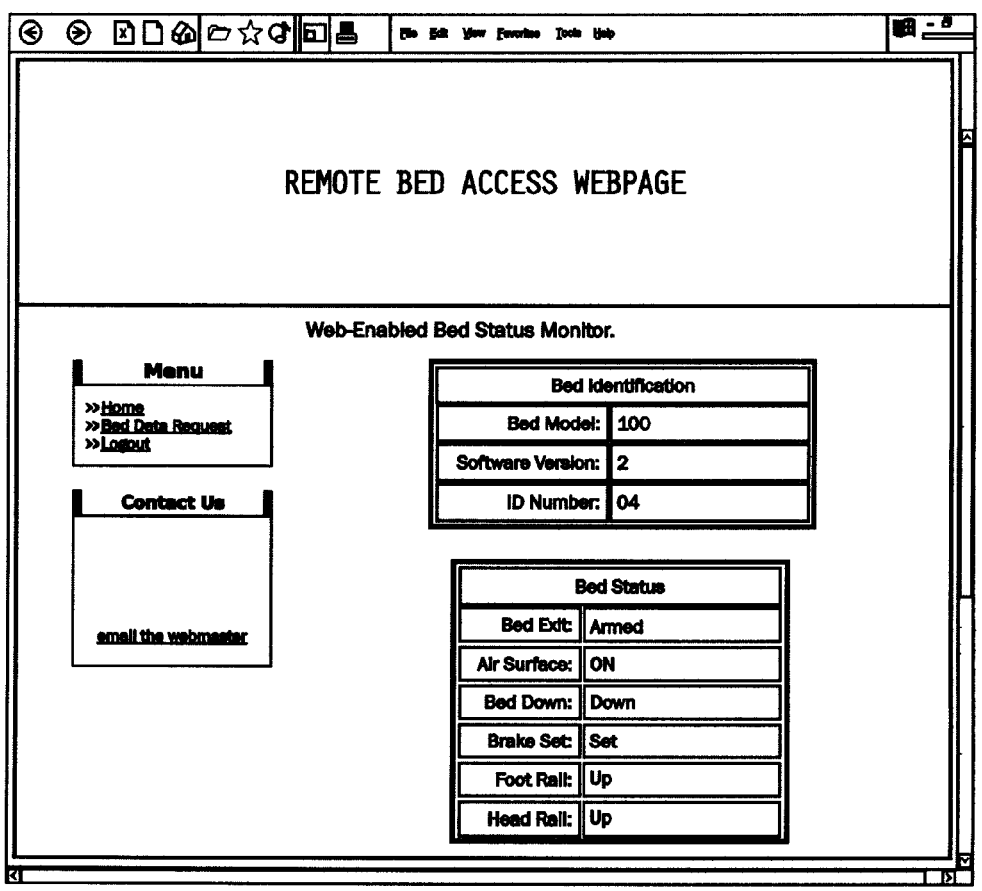
FIG. 16D is a screen shot of a healthcare device status monitor webpage associated with the webserver interface of the system of FIG. 1.

At step 708, the processor 56 provides a home webpage indicating successful login, for example, as shown in the screen shot of FIG. 16C. At step 712, the processor 56 determines whether the user has requested a hyperlink to another webpage provide by the webserver 54. If so, one of the steps, 718, 720, 722, 724, and 726 is executed. At step 714, the processor 56 retrieves the XML variables as were previously defined above. At step 716, the processor 56 uses an XML process to provide the variables to the appropriate webpages, for example, as associated with step 718 and step 720 described below. At step 718, the processor 56 determines that a bed status monitor webpage has been requested and is provided, for example, as shown in the screen shot of the webpage of FIG. 16D. At step 728, the broadcast bed data displayed by the illustrative webpage of FIG. 16D can be viewed by the user.

Figure 16E:
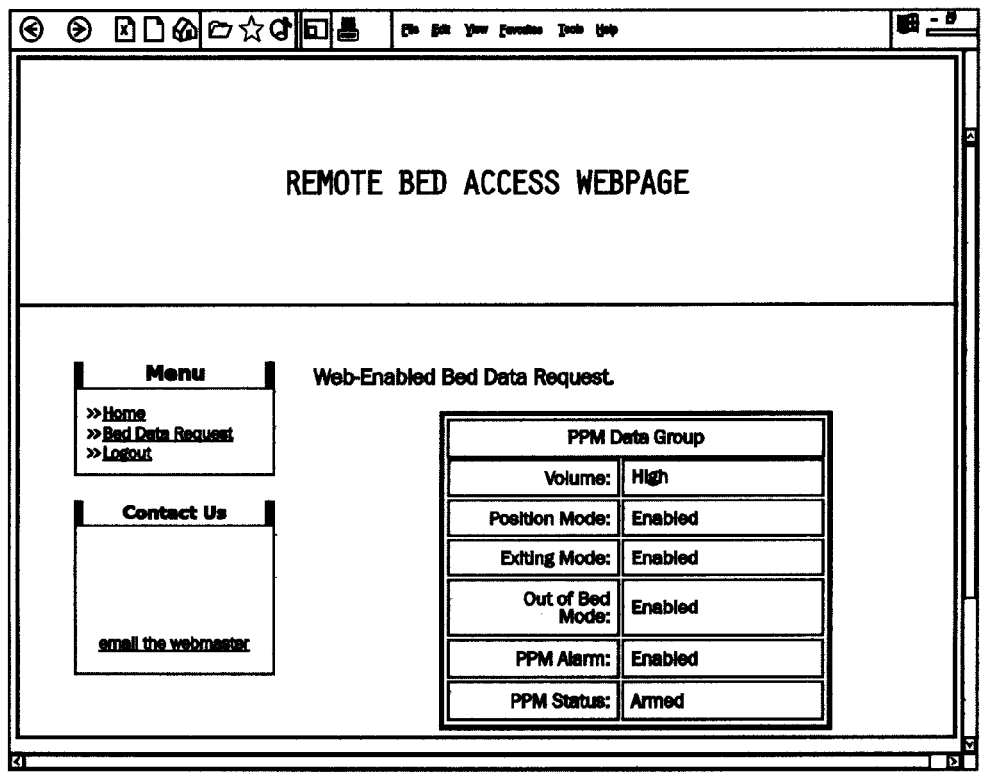
FIG. 16E is a screen shot of a requested healthcare device data webpage associated with the webserver interface of the system of FIG. 1.

At step 720, the processor 56 determines that the user has requested specific data group, for example, the PPM datagroup shown in the screen shot of the webpage of FIG. 16E. At step 730, the processor determines which datagroup has been requested by the user. Depending on the group requested in step 730, execution of the algorithm 700 continues at one of steps 732, 734, 736, and 738. The steps respectively provide data relating to GROUP_PPM, GROUP_FRAME, GROUP_SURFACE, and GROUP_BATTERY. At step 740, the user can view the requested bed data group.

Figure 16F:
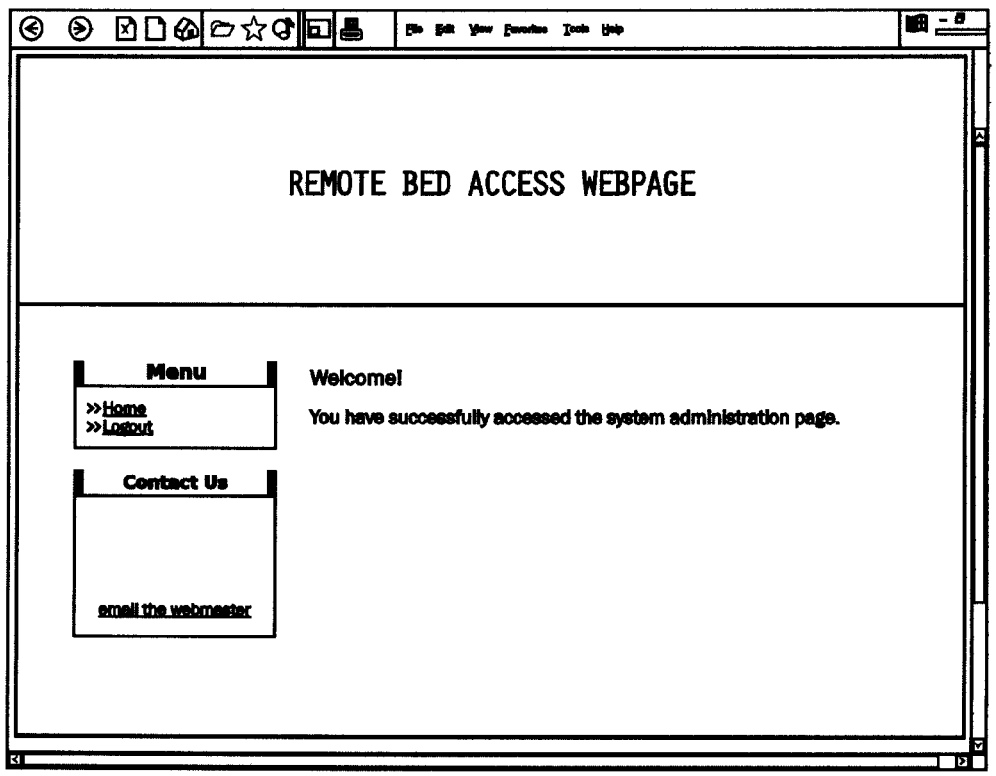
FIG. 16F is a screen shot of an administration webpage associated with the webserver interface of the system of FIG. 1.

At step 722, the administration webpage is provided by the processor 56, for example, the screen shot according to FIG. 16F.

Figure 16G:
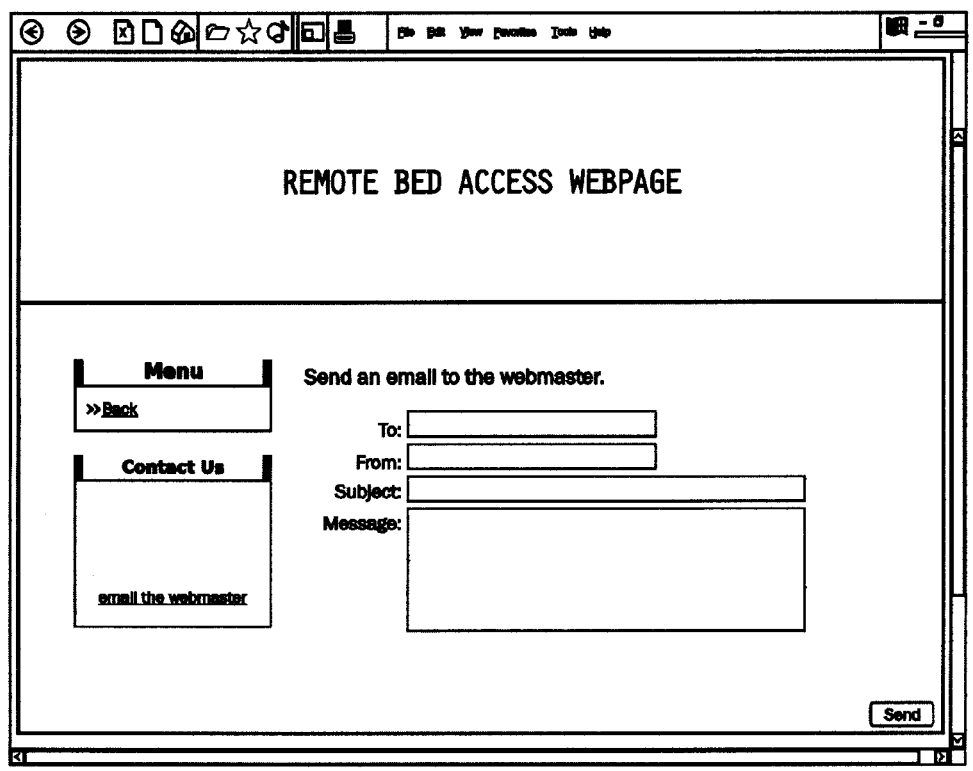
FIG. 16G is a screen shot of an e-mail webpage associated with the webserver interface of they system of FIG. 1.

At step 724, the processor 56 provides an e-mail webpage, for example, according to the screen shot shown in FIG. 16G. At step 744, the processor 56 allows the user to create and send an e-mail to the webmaster or other recipient associated with the website.

Figure 16H:
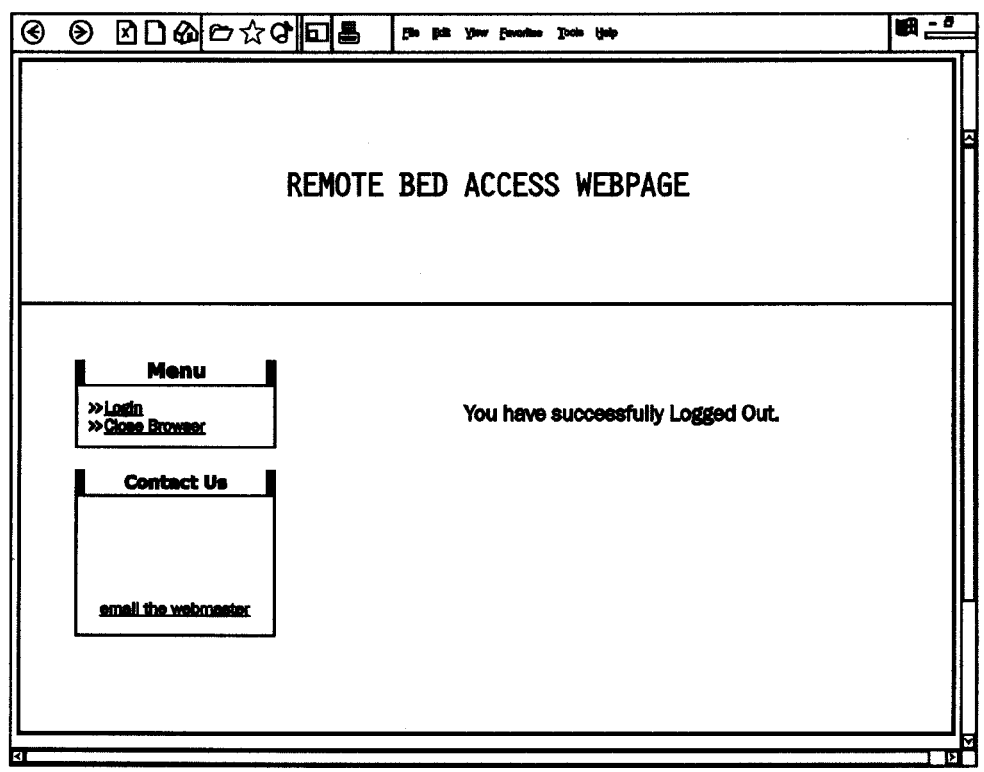
FIG. 16H is a screen shot of a logged out webpage associated with the webserver interface of the system of FIG. 1.

At step 726, the processor 56 provides a logout of the user, for example, as shown in the screen shot of FIG. 16H. At step 746, the processor 56 logs the user out of the webserver 54. Alternatively, the processor 56 in algorithm 700 can be configured to operate on and output other forms of XML or non-XML data, code or files.

Figure 12:
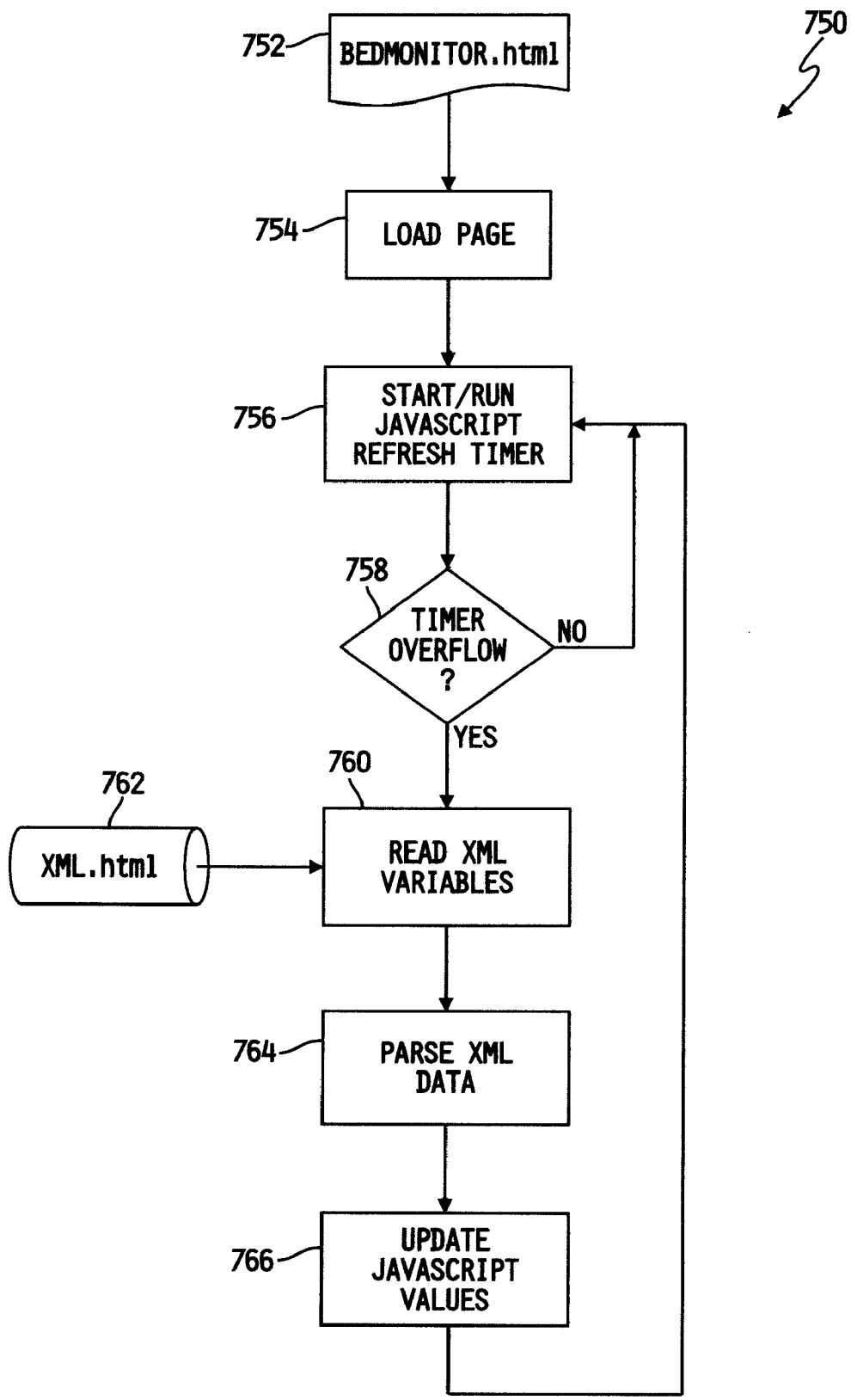
FIG. 12 is a flowchart of a software algorithm associated with the webserver interface of the system of FIG. 1 and for processing data broadcast by the patient support system.

Referring now to FIG. 12, a flowchart is shown for one illustrative embodiment of a software algorithm 750 for processing the data transmitted by the bed communication device 46 to the webserver 54. At step 752, the processor 56 provides the bed monitor webpage, for example, according to the illustrative screen shot of FIG. 16D. At step 754, the processor 56 loads the webpage. At step 756, the processor 56 starts and/or runs the javascript refresh timer for dynamically refreshing the XML variables associated with the webpage.

At step 758, the processor 56 determines whether the refresh timer has exceeded a preset overflow. If so, then execution of the algorithm 750 continues at step 760, otherwise execution returns to step 756. At step 760, the processor 56 reads the XML variables into the webpage from the XML variables as illustrated in step 762. At step 764, the processor 56 parses the XML data. At step 764, the javascript values are updated with the XML data. After step 764 is completed, execution of the algorithm 750 continues at step 756. Alternatively, the processor 56 in algorithm 750 can operate on and output other forms of XML or non-XML data, code or files other than XML variables and webpages.

Figure 13:
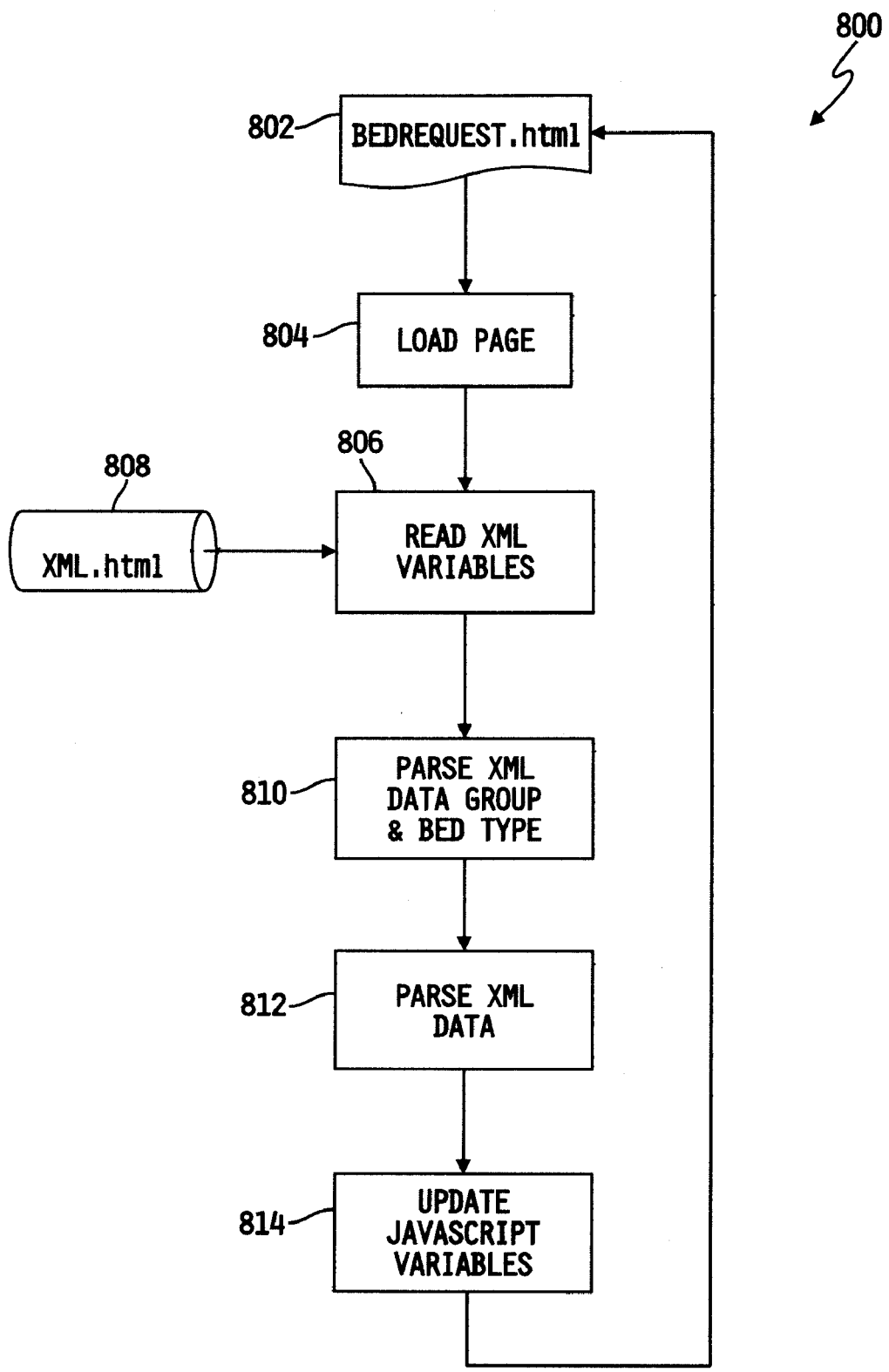
FIG. 13 is a flowchart of a software algorithm associated with the webserver interface of the system of FIG. 1 and for processing of data requested from the patient support system.

Referring now to FIG. 13, a flowchart is shown to illustrate one illustrated embodiment of a software algorithm or routine for providing data to a webpage that is requested by a web user. Specifically, algorithm 800 begins at step 802 and processor 56 provides a bed request data webpage, for example, the illustrative screen shot of FIG. 16E. At step 804, the processor 56 loads the webpage. At step 806, the processor 56 reads the XML variables, for example, as illustrated by step 808. At step 810, the processor 56 parses the XML data group and bed type. At step 812, the processor 56 parses the XML data. At step 814, the processor 56 updates to javascript variables with the parsed XML data in order to dynamically refresh the requested bed data group. After execution of step 814, execution of the algorithm 800 returns to step 802. Alternatively, the processor 56 in algorithm 800 can operate on and output other forms of XML or non-XML data, code or files other than XML variables and webpages.

The algorithms 700, 750, and 800 can also include steps to provide webpage display or another user receivable output of diagnostic and other information, including, for example, analysis results, bed status, service or component orders and status, and other such information that is a function of at least the diagnostic information.

Figure 14:
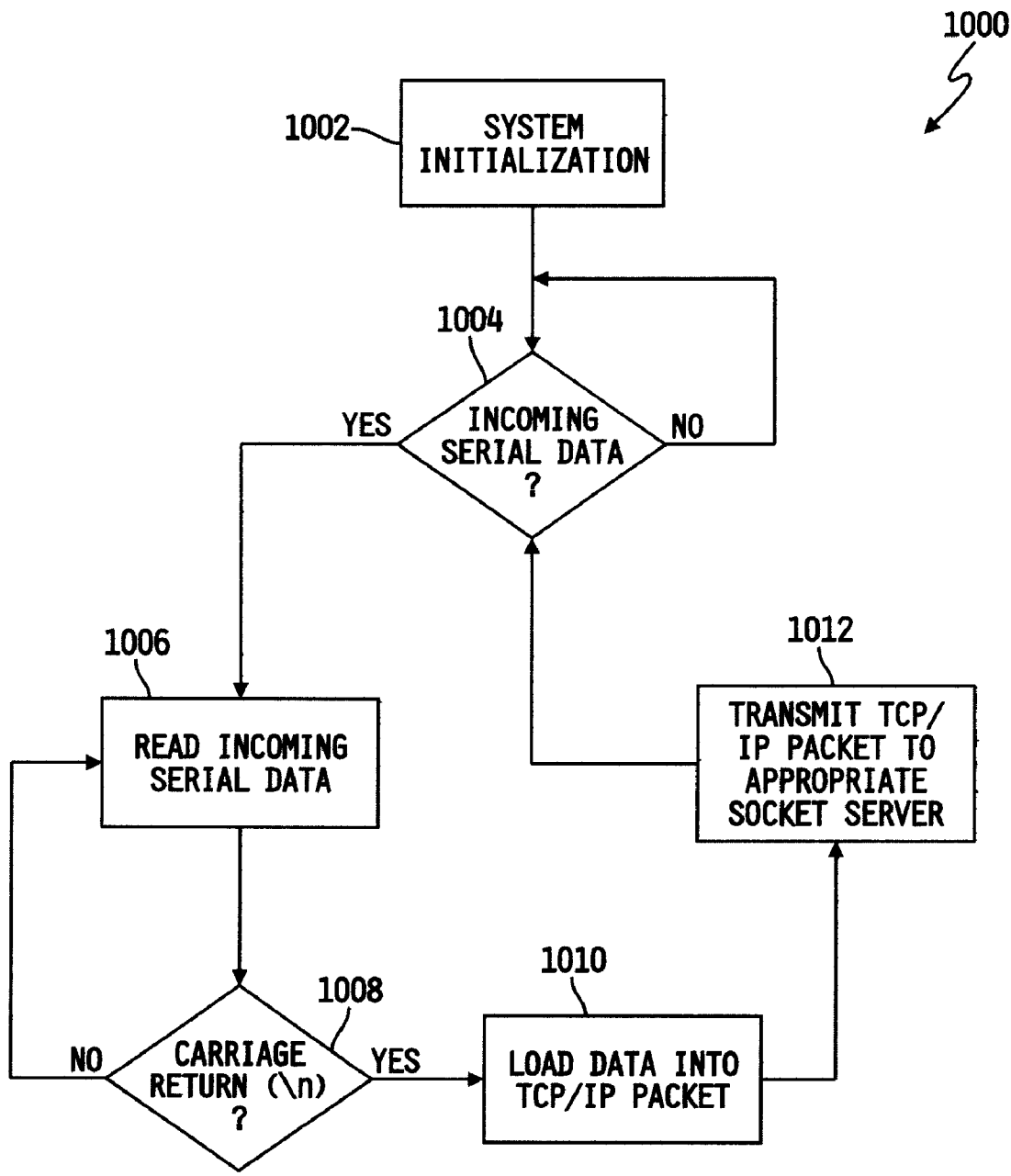
FIG. 14 is a flowchart of a software algorithm associated with the network interface of the system of FIG. 1.

Referring now to FIG. 14, a flowchart is shown for one illustrative embodiment of a software algorithm for controlling an embodiment of system 30 having a network interface 1054. The algorithm 1000 is executed by processor 1056 of network interface 1054. The algorithm 1000 begins at step 1002. At step 1002, the processor 1056 initializes the hardware and/or software of network interface 1054. At step 1004, the processor 1056 determines whether or not data has been received from the communication interface 48. If so, step 1006 is executed, else step 1012 is executed. At step 1006, the processor 1056 obtains a segment, for example, a byte, of the received data. At step 1008, the processor 1056 determines whether the segment contains an end of message code, for example, the ASCII code for a carriage return. If so, step 1010 is executed, else step 1006 is executed to obtain another segment of received data. At step 1010, the processor 1056 converts the received message to a TCP/IP packet for transmission. At step 1012, the processor 1056 transmits the TCP/IP pack to a predefined or earlier specified socket server. For example, the socket server could specify bed server 76 or monitoring device 38.

Figure 15:
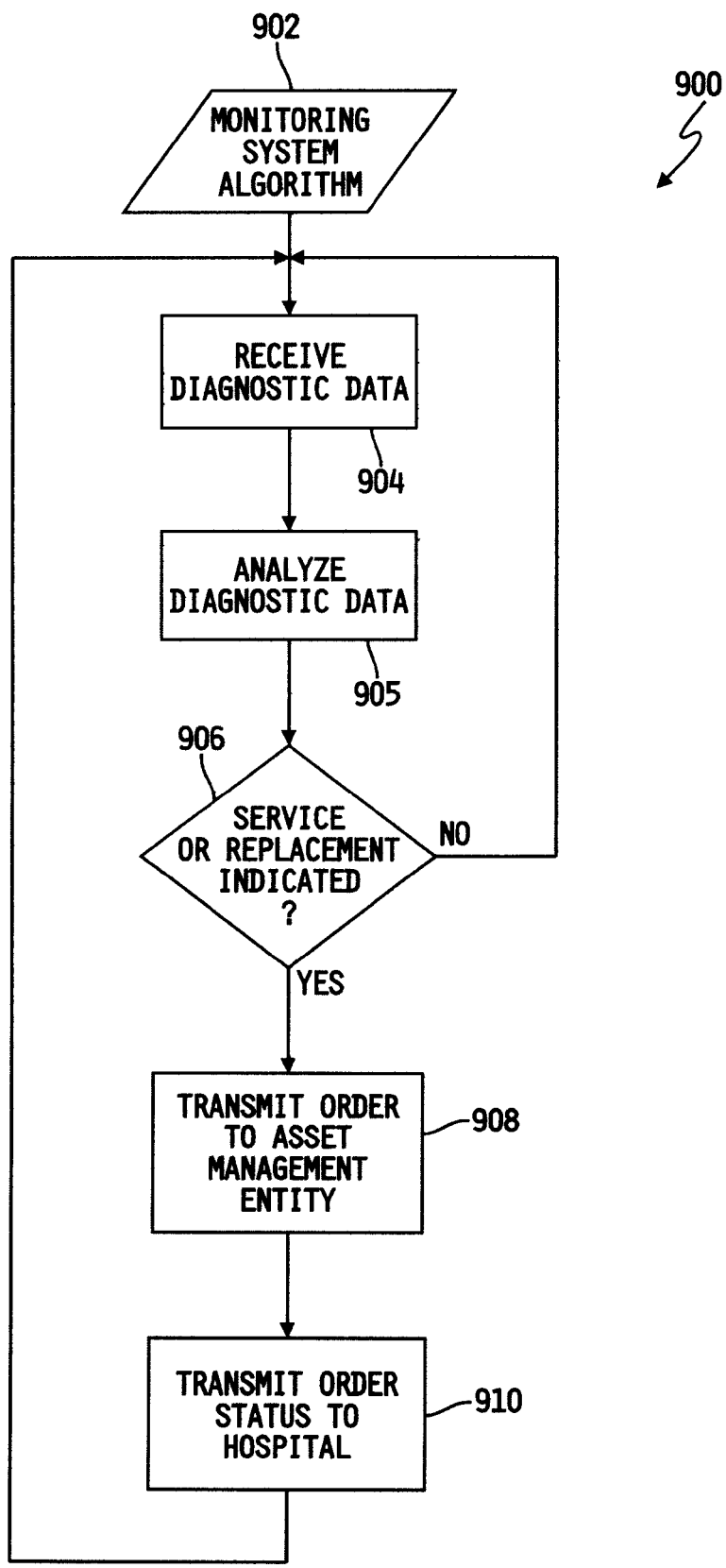
FIG. 15 is a flowchart of a software algorithm associated with the remote monitoring system of the system of FIG. 1 and for determining and communicating service or replacement relating to the healthcare device.

Referring now to FIG. 15, a flowchart is shown of one illustrated embodiment of a software algorithm for providing geographically remote diagnostic and automatic and/or manual service or replacement management of the patient support system 32. The algorithm 900 is executed, for example, by a processor 82 of the monitoring device 38, located at remote location 42, which is geographically remote from patient support system 32.

In step 904, the processor 82 receives the data transmitted by the bed communication device 46. The data can be received based on a broadcast of diagnostic information from the bed server 76 or the communication interface 48, or as a result of the processor 82 periodically polling the bed server 76 or the communication interface 48. At step 905, the processor 82 analyzes the received data. For example, in order to identify and report preventative or responsive service requirements, the processor 82 can use real-time and historical data, probabilistic methods, performance trends of an individual device and/or relative to other devices, and thresholds for diagnostic information. At step 906, the monitoring device determines whether service or replacement of a component or the complete patient support system 32 is indicated based on the analysis of the data received. If so, execution of the algorithm 900 continues at step 908, otherwise execution returns to step 904.

At step 908, the processor 82 transmits the status of the patient support system 32 and/or a service and/or parts order to an asset management entity 40 based on the indicated service or replacement. At step 910, the processor 82 transmits a status of the patient support system 32 and/or a service/parts order to the hospital or other user of the bed to be serviced or replaced. After step 910 is completed, execution of the algorithm 900 continues at step 904.

Although certain illustrative embodiments have been described in detail above, variations and modifications exist within the scope and spirit of this disclosure as described and as defined in the following claims.

The invention claimed is:

1. A remote diagnostic monitoring system for a patient support system, the remote diagnostic monitoring system comprising:
    a sensor system coupled to the patient support system and configured to generate sensor data relating to at least one parameter of the patient support system;
    a communication adapter coupled to the sensor system and configured to transmit the sensor data;
    a nurse call system coupled to the patient support system via the communication adapter; and
    a monitoring device located geographically distant from the patient support system, coupled to the communication adapter by a first datalink, and configured to receive the sensor data and determine a diagnostic status of the patient support system based on the received sensor data, wherein the monitoring device transmits updated firmware to the patient support system via the communication adapter for changing programming of the patient support system, wherein at least some of the sensor data generated by the sensor system is communicated to the nurse call system via the communication adapter, wherein the monitoring device receives a user request for a specific subset of data from among a plurality of available subsets of data, wherein the monitoring device communicates the user request to the patient support system via the communication adapter and the patient support system responds to the user request by transmitting to the monitoring device via the communication adapter the specific subset of data without transmitting other subsets of data of the plurality of available subsets of data, wherein the specific subset of data relates to at least one of a position of a portion of a bed frame and a feature of an air mattress.

2. The remote diagnostic monitoring system of claim 1, wherein the first datalink includes at least one of a telecommunication network and the Internet.

3. The remote diagnostic monitoring system of claim 1, further comprising a second datalink coupling the sensor system and the communication adapter.

4. The remote diagnostic monitoring system of claim 3, wherein the second datalink includes a wireless communication connection.

5. The remote diagnostic monitoring system of claim 3, wherein the communication adapter is configured to convert the sensor data from a first protocol used by the sensor system to a second protocol used by at least one of the first data link, the second data link, and the monitoring device.

6. The remote diagnostic monitoring system of claim 5, wherein the second protocol includes at least one of XML and TCP/IP.

7. The remote diagnostic monitoring system of claim 3, wherein the first datalink further includes a healthcare facility network and a server of the healthcare facility network.

8. The remote diagnostic monitoring system of claim 1, wherein the communication adapter includes at least one of a webserver and network portal.

9. The remote diagnostic monitoring system of claim 1, wherein the sensor data relates to at least one of vibration, displacement, rate, component temperature, ambient temperature, component humidity, ambient humidity, thermal loading, pressure, noise, mechanical load, current, voltage, electrical power, signal signature, calibration values, transit time, fault rate, logic or communication error, and accumulated usage.

10. The remote diagnostic monitoring system of claim 1, wherein the sensor system monitors at least one of a drive, a user control, a caregiver control, an air system, a movable member, a power supply, a battery, a load cell, control logic, a communication circuit, a sensor and a cycle counter.

11. The remote diagnostic monitoring system of claim 1, wherein the monitoring device is configured to determine based on the sensor data whether service or replacement of the healthcare device or a portion thereof is indicated.

12. The remote diagnostic monitoring system of claim 11, wherein the monitoring device is configured to transmit a message relating to service or replacement of the healthcare device to the healthcare facility where the healthcare device is located.

13. The remote diagnostic system of claim 1, wherein the communication adapter comprises a first protocol converter coupled to the patient support system and configured for transmission and protocol conversion of diagnostic information between a first communication protocol used by the patient support system and a second communication protocol; and a communication device configured to receive the diagnostic information and transmit the diagnostic information to the remote monitoring device.

14. The remote diagnostic system of claim 13, wherein the communication adapter further comprises a second protocol converter coupled to the first protocol converter and configured for transmission and protocol conversion of diagnostic information between the second communication protocol and a third communication protocol.

15. The remote diagnostic system of claim 13, wherein the diagnostic information relates to a parameter of a component of the patient support system, the parameter relating to at least one of vibration, displacement, rate, component temperature, ambient temperature, component humidity, ambient humidity, thermal loading, pressure, noise, mechanical load, current, voltage, electrical power, signal signature, calibration values, transit time, fault rate, logic or communication error, and accumulated usage.

16. The remote diagnostic system of claim 13, wherein the diagnostic information relates to at least one of a status of a drive, a user control, a caregiver control, an air system, a movable member, a power supply, a battery, a load cell, control logic, a communication circuit, a sensor, and a cycle counter.

17. A method of remotely monitoring a hospital bed, comprising:
    sensing with a sensor of the hospital bed data relating to at least one parameter of the hospital bed;
    converting with a communication interface the data for transmission;
    transmitting from the communication interface the data over a telecommunication network;
    receiving the data in a computer device at a geographically remotely located monitoring system that is coupled to the telecommunication network;
    receiving in a nurse call system at least some of the data transmitted from the communication interface; and
    determining with the computer device based on the received data whether service or replacement of the hospital bed is indicated, wherein the computer device transmits updated firmware to the hospital bed via the communication interface for changing programming of the hospital bed, wherein the computer device receives a user request for a specific subset of data from among a plurality of available subsets of data, wherein the computer device communicates the user request to the patient support system via the communication adapter and the patient support system responds to the user request by transmitting to the computer device via the communication adapter the specific subset of data without transmitting other subsets of data of the plurality of available subsets of data, wherein the specific subset of data relates to at least one of a position of a portion of a bed frame and a feature of an air mattress.

18. The method of claim 17, further comprising transmitting a message relating to service or replacement of the hospital bed to a healthcare facility where the hospital bed is located.

19. The method of claim 17, further comprising transmitting to a healthcare asset management entity an order for one of service or replacement of the hospital bed.

20. The method of claim 17, wherein the data relates to at least one of a vibration, a displacement, a rate, a component temperature, an ambient temperature, a component humidity, an ambient humidity, a thermal loading, a pressure, a noise, a mechanical load, a current, a voltage, an electrical power, a signal signature, a calibration values, a transit time, a fault rate, a logic or communication error, an accumulated usage, a drive, a user control, a caregiver control, an air system, a movable member, a power supply, a battery, a load cell, control logic, a communication circuit, a sensor, and a cycle counter.

* * * * *